(12) United States Patent
Minekawa et al.

(10) Patent No.: US 9,176,124 B2
(45) Date of Patent: Nov. 3, 2015

(54) METHOD FOR MEASUREMENT OF EQUOL IN BIOLOGICAL SAMPLE BY IMMUNOASSAY, KIT FOR THE MEASUREMENT, AND METHOD FOR DETERMINATION OF EQUOL PRODUCTION ABILITY OF SUBJECT

(75) Inventors: Takayuki Minekawa, Otawara (JP); Kumiko Shindome, Otawara (JP); Katsushi Abe, Otawara (JP); Hiroshi Okuma, Otawara (JP); Chieko Ando, Osaka (JP); Yasuhiro Abiru, Osaka (JP)

(73) Assignees: OTSUKA PHARMACEUTICAL CO., LTD., Tokyo (JP); EIKEN KAGAKU KABUSHIKI KAISHA, Tokyo (JP)

( * ) Notice: Subject to any disclaimer, the term of this patent is extended or adjusted under 35 U.S.C. 154(b) by 815 days.

(21) Appl. No.: 13/318,735

(22) PCT Filed: May 11, 2010

(86) PCT No.: PCT/JP2010/057974
§ 371 (c)(1),
(2), (4) Date: Nov. 3, 2011

(87) PCT Pub. No.: WO2010/131660
PCT Pub. Date: Nov. 18, 2010

(65) Prior Publication Data
US 2012/0064550 A1    Mar. 15, 2012

(30) Foreign Application Priority Data

May 11, 2009    (JP) .................................. 2009-114572

(51) Int. Cl.
*G01N 33/00*    (2006.01)
*G01N 33/53*    (2006.01)
*C07K 16/44*    (2006.01)

(52) U.S. Cl.
CPC ............ *G01N 33/5308* (2013.01); *C07K 16/44* (2013.01)

(58) Field of Classification Search
None
See application file for complete search history.

(56) References Cited

U.S. PATENT DOCUMENTS 5,420,016 A * 5/1995 Boguslaski et al. ............ 435/12
2004/0235758 A1   11/2004 Setchell et al.

FOREIGN PATENT DOCUMENTS

| JP | 2006-504409 | A  | 2/2006 |
| JP | 2006-242602 | A  | 9/2006 |
| JP | 2006-296434 | A  | 11/2006 |
| WO | 2004/009035 | A2 | 1/2004 |

OTHER PUBLICATIONS

Setchell et al., The Pharmacokinetics of S-(−)Equol Administered as SE5-OH Tablets to Healthy Postmenopausal Women, The Journal of Nutrition, Sep. 23, 2009, pp. 2037-2043.*
Zubik et al., Bioavailability of soybean isoflavones from aglycone and glucoside forms in American women, Am J Clin Nautr 2003; 77, pp. 1459-1465.*
Reimer et al., Comparison of a Time-Resolved Fluorescence Immunoassay and an Enzyme-Linked Immunosorbent Assay for the Analysis of Atrazine in Water, J Agric. Food Chem. 1998, 46, pp. 3353-3358).*
Kopec et al., Separation and Isolation of (S)-Equol: The Biologically Relevent Metabolite of the Isoflavone Daidzein, Undergraduate Thesis, The Ohio State University, 2006, pp. 1-19.*
*Physiological Sciences Progress*, vol. 37, No. 4, pp. 359-361, 2006.
Paul I. Creeke et al, Development of ELISAs for the Measurement of the Dietary Phytoestrogens Diadzein and Equol in Human Plasma, *Food and Agricultural Immunology* (1998), vol. 10, pp. 325-337.
C. Bennetau-Pelissero et al, ELISA as a new method to measure genistein and daidzein in food and human fluids, *Food Chemistry*, vol. 82 (2003), pp. 645-658.
Talbot, Duncan C.S., et al., "Monoclonal Antibody-Based Time-Resolved Fluorescence Immunoassays for Daidzein, Genistein, and Equol in Blood and Urine: Application to the Isoheart Intervention Study", Clinical Chemistry, 2007, pp. 748-756, vol. 53, No. 4.
Brouwers, Elke, et al., "Time-resolved fluoroimmunoassay for equol in plasma and urine", The Journal of Steroid Biochemistry & Molecular Biology, 2003, pp. 577-588, vol. 84, Issue 5.
Suzuki, Toshimi, et al., "Estrogen-Like Effect of S-equol in Ovariectomized Rats", Saga Nutraceuticals Research Institute, Otsuka Pharmaceutical Co., Ltd., Abstract for the 61st Meeting of the Japanese Society of Nutrition and Food Science, 2007, p. 250, 4K-6p.
Setchell, Kenneth D.R., "S-Equol, a potent ligand for estrogen receptor β, is the exclusive enantiomeric form of the soy isoflavone metabolite produced by human intestinal bacterial flora[1-4]", The American Journal of Clinical Nutrition, 2005, pp. 1072-1079, vol. 81.
Frankenfeld, Cara L., et al., "Serum steroid hormones, sex hormone-binding globulin concentrations, and urinary hydroxylated estrogen metabolites in post-menopausal women in relation to daidzein-metabolizing phenotypes", Journal of Steroid Biochemistry & Molecular Biology, 2004, pp. 399-408, vol. 88.
Setchell, Kenneth D.R., et al., "Method of Defining Equol-Producer Status and Its Frequency among Vegetarians[1,2]", The Journal of Nutrition, Nutrient Physiology, Metabolism, and Nutrient-Nutrient Interactions, 2006, pp. 2188-2193.

(Continued)

*Primary Examiner* — Gary W Counts
(74) *Attorney, Agent, or Firm* — Sughrue Mion, PLLC

(57) ABSTRACT

The determination method of the present invention includes steps of measuring equol in a biological sample derived from a subject who has ingested soybean isoflavone by an immunological method using S-equol as at least one antigen selected from the group consisting of the standard antigen and the labeled antigen, and determining an equol-producing ability of the subject based on the measured value of equol obtained in the above step.

10 Claims, 8 Drawing Sheets

(56) References Cited

OTHER PUBLICATIONS

Susan Dentith et al., Development of Techniques for the Analysis of Isoflavones in Soy Foods and Nutraceuticals, Current Opinion in Clinical Nutrition and Metabolic Care, vol. 11, No. 3, pp. 242-247 (2008).

Supplemental European Search Report dated Oct. 4, 2012 in European Application No. 10774917.8.

Setchell, Kenneth D.R., et al., "The Clinical Importance of the Metabolite Equol—A Clue to the Effectiveness of Soy and Its Isoflavones", The Journal of Nutrition, American Society for Nutritional Sciences, vol. 132 No. 12, 2002, pp. 3577-3584.

"Development of Research of Detection Methods for Soybean Isoflanones", Tianjin Pharmacy, vol. 20 No. 2, Apr. 2008, 4 pages.

"A development of the study on the detection of soy isoflavones", TianJin Pharmacy, vol. 20, No. 2, Apr. 2008, 4 pages total, English portions only.

\* cited by examiner

METHOD FOR MEASUREMENT OF EQUOL IN BIOLOGICAL SAMPLE BY IMMUNOASSAY, KIT FOR THE MEASUREMENT, AND METHOD FOR DETERMINATION OF EQUOL PRODUCTION ABILITY OF SUBJECT

TECHNICAL FIELD

The present invention relates to a method for measuring equol in a biological sample by an immunological method, a kit for the measurement, and a method for determining equol-producing ability of a subject.

BACKGROUND ART

Isoflavones contained in soybeans are widely known to have the effect (the anti-estrogenic effect) of preventing breast cancer, prostate cancer, and the like; as well as the effect (the estrogen-like effect) of ameliorating menopause symptoms, postmenopausal diseases such as osteoporosis, hyperlipidemia, hypertension, and the like.

In addition to the direct clinical effects of soybean isoflavones, recent reports suggest that equol, which is an active metabolite of the soybean isoflavones, is the key to effectiveness in clinical applications, instead of the soybean isoflavones. Specifically, various reports state that equol is effective against breast cancer, prostate cancer, menopause symptoms, and postmenopausal osteoporosis.

Further, it has been reported that because equol is produced by intestinal bacteria, the amount of production is different depending on intestinal flora, and thus varies among different individuals. Accordingly, it is undeniable that there are some individuals who cannot experience a desired anti-estrogenic effect and estrogen-like effect, even if they ingest soybean processed products.

Some time later, lactic acid bacteria that efficiently produce equol were isolated and identified (Patent Literature 1). An efficient intake of equol into the body is expected to be achieved by orally ingesting a lactic acid bacteria preparation, and allowing the lactic acid bacteria to reach or colonize in the intestine. At this time, it is possible to confirm whether the lactic acid bacteria have reached or colonized in the intestine by measuring equol in, for example, urine, blood, feces, etc.

The following methods are known as methods to measure equol: a method using a liquid chromatograph-mass spectrometer or a gas chromatograph-mass spectrometer in the case of blood samples, and a method using instrumental analysis such as high-performance liquid chromatography (HPLC), etc. in the case of urine samples. However, a simpler measurement method is demanded.

Further, as for the methods for measuring equol by immunoassay, Labmaster TR-FIA Research Reagents for the Measurement of Equol, which uses time-resolved fluoroimmunoassay, is commercially available (NPL 1).

Meanwhile, the presence of two types of diastereoisomers of equol, i.e., S-equol and R-equol, is known. Between them, S-equol is the only metabolite produced from daidzein (a precursor of equol) by intestinal bacteria. Further, S-equol binds with an estrogen-receptor much more strongly (NPL 2).

Specifically, S-equol is the equol that indicates its presence in vivo, and that is contained in blood samples and urine samples; it is thus useful to specifically measure S-equol.

CITATION LIST

Patent Literature

[PTL 1] Japanese Unexamined Patent Publication No. 2006-296434

Non-Patent Literatures

[NPL 1] E. Brouwers, et al. Journal of Steroid Biochemistry & Molecular Biology, 2003, Vol. 84, pp. 577-588
[NPL 2] K. D. R. Setchell, et al. The American Journal of Clinical Nutrition, 2005, Vol. 81, pp. 1072-1079

SUMMARY OF INVENTION

Technical Problem

An object of the present invention is to develop a method for specifically and accurately measuring S-equol, in a method for measuring equol by an immunological method, i.e., immunoassay. Another object of the present invention is to develop a kit capable of specifically and accurately measuring S-equol when measuring the concentration of equol by an immunological method. Still another object of the present invention is to develop a method for determining an equol-producing ability of a subject.

Technical Solution

Factors that greatly affect the performance of immunoassay include the identity or similarity between a target substance in a sample and a standard substance used for determining the concentration from a reaction of the target substance with its binding partner; or between a target substance in a sample and a competitive substance used in a competition reaction.

Accordingly, S-equol was used as a standard substance for preparing a standard curve to obtain measured values. As a result, the accuracy of the measured values was improved.

Further, labeled S-equol was used as a competing reactant in immunoassay that uses competitive immunoreaction. As a result, nonspecific reactions were suppressed, and the range of accurate measurement was expanded, compared to when a mixture of S-equol and R-equol was used.

The present invention is accomplished as a result of further studies based on the above findings.

Specifically, the present invention comprises the following:

Item 1. A method for measuring equol in a biological sample by an immunological method, comprising using S-equol as at least one antigen selected from the group consisting of a standard antigen used for the preparation of a standard curve and a labeled antigen that competes with equol in a biological sample.

Item 2. The method according to Item 1 comprising using, as a primary antibody, an anti-equol antibody whose cross-reactivity with daidzein is 10% or less; cross-reactivity with genistein is 10% or less; cross-reactivity with glycitein is 10% or less; cross-reactivity with dihydrodaidzein is 20% or less; and cross-reactivity with dehydroequol is 20% or less, when the cross-reactivity with S-equol is assumed to be 100%.

Item 3. The method according to Item 1, wherein a labeling substance in the labeled antigen is at least one member selected from the group consisting of enzymes, radioisotopes, dyes, fluorescent materials, latexes, and metal colloids.

Item 4. The method according to Item 1, wherein the immunological method is at least one type selected from the group consisting of ELISA, radioimmunoassay, and immunochromatographic assay.

Item 5. The method according to Item 1, wherein the biological sample is at least one member selected from the group consisting of urine and blood.

Item 6. The method according to Item 1, wherein an equol conjugate in the biological sample is measured without being deconjugated.

Item 7. A kit for measuring equol in a biological sample by an immunological method, comprising S-equol as at least one antigen selected from the group consisting of a standard antigen used for the preparation of a standard curve and a labeled antigen that competes with equol in a sample.

Item 8. The kit according to Item 7 further comprising, as a primary antibody, an anti-equol antibody whose cross-reactivity with daidzein is 10% or less; cross-reactivity with genistein is 10% or less; cross-reactivity with glycitein is 10% or less; cross-reactivity with dihydrodaidzein is 20% or less; and cross-reactivity with dehydroequol is 20% or less, when the cross-reactivity with S-equol is assumed to be 100%.

Item 9. The kit according to Item 7, wherein the immunological method is at least one type selected from the group consisting of ELISA, radioimmunoassay, and immunochromatographic assay.

Item 10. The kit according to Item 7, wherein the biological sample is at least one member selected from the group consisting of urine and blood.

Item 11. A method for determining an equol-producing ability of a subject, comprising the steps of
(1) measuring equol in a biological sample derived from a subject who has ingested soybean isoflavone, by an immunological method using S-equol as at least one antigen selected from the group consisting of a standard antigen used for preparation of a standard curve, and a labeled antigen that competes with equol in the biological sample; and
(2) determining an equol-producing ability of the subject based on the measuredtvalue of equol obtained in step (1).

Item 12. The determination method according to Item 11, wherein, in step (1), an equol conjugate in the biological sample is measured without being deconjugated.

Advantageous Effects of Invention

With the implementation of the measurement method of the present invention, it is possible to suppress nonspecific reactions and obtain accurate measurement results in a method for measuring equol in a biological sample by immunoassay. Additionally, the method can further be simply implemented with the use of the kit of the present invention. Moreover, whether a subject has an equol-producing ability can be accurately and simply determined according to the determination method of the present invention.

Additionally, the concentration of equol measured by the present invention indicates high correlation with the concentration of equol measured by HPLC. Further, the present invention takes only about 3 hours to detect the concentration, and can quickly measure the concentration of equol, compared to HPLC, which takes 72 hours, or about 2 weeks in the case of commission work. Additionally, the kit of the present invention costs much less than HPLC, yet can provide the same level of detection sensitivity as HPLC.

Further, according to the present invention, the presence and the level of the equol-producing ability of a subject can be accurately, simply, and quickly determined with high specificity. Therefore, based on the measurement results and the determination results, it is possible to understand the possible onset of diseases and the level of symptoms of, the diseases (for example, breast cancer, prostate cancer, and menopause symptoms; as well as postmenopausal osteoporosis, hyperlipidemia, hypertension, etc.) associated with the lack of the equol-producing ability. Consequently, these diseases can be appropriately prevented and ameliorated.

DESCRIPTION OF EMBODIMENTS

Figure 1:
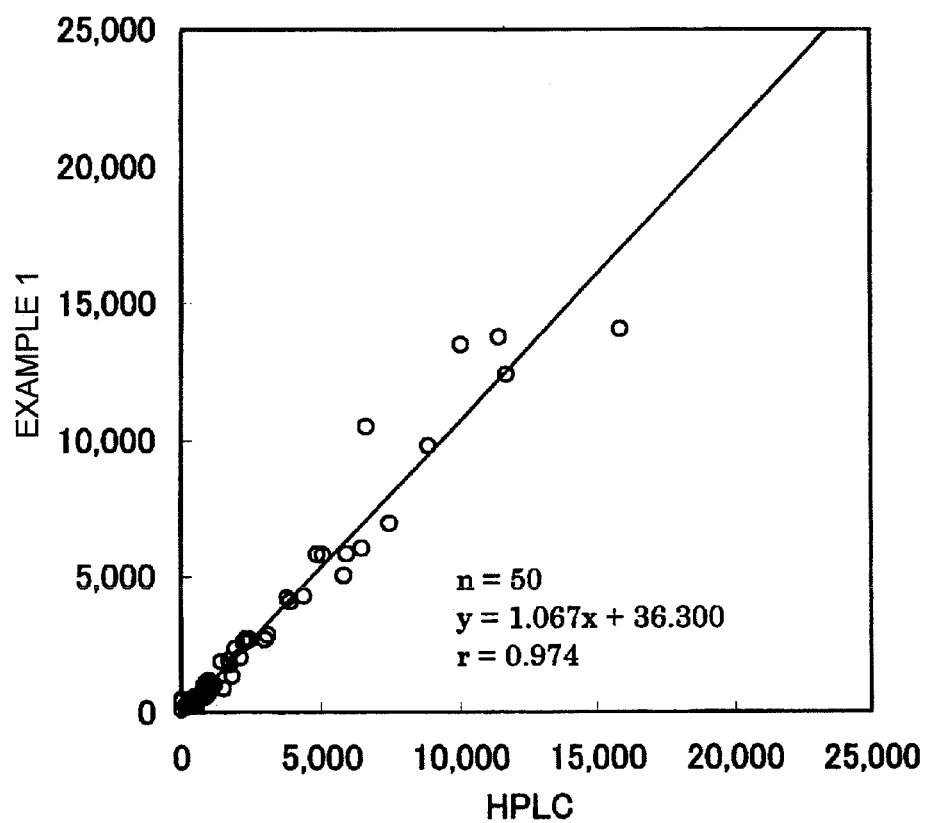
FIG. 1 is a correlation diagram showing the results measured by HPLC and in Example 1. In the diagram, the vertical axis indicates values obtained by ELISA, and the horizontal axis indicates values obtained by HPLC. The unit is ng/mL in each case.
Figure 2:
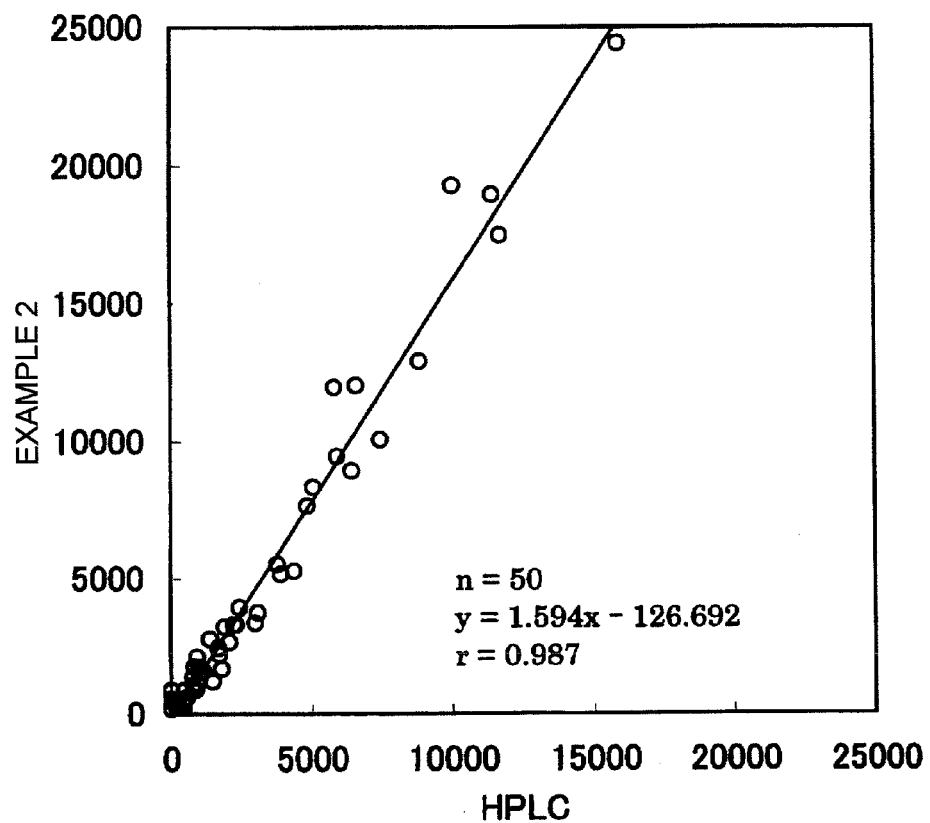
FIG. 2 is a correlation diagram of results measured by HPLC and in Example 2. In the diagram, the vertical axis indicates values obtained by ELISA, and the horizontal axis indicates values obtained by HPLC. The unit is ng/mL in each case.
Figure 3:
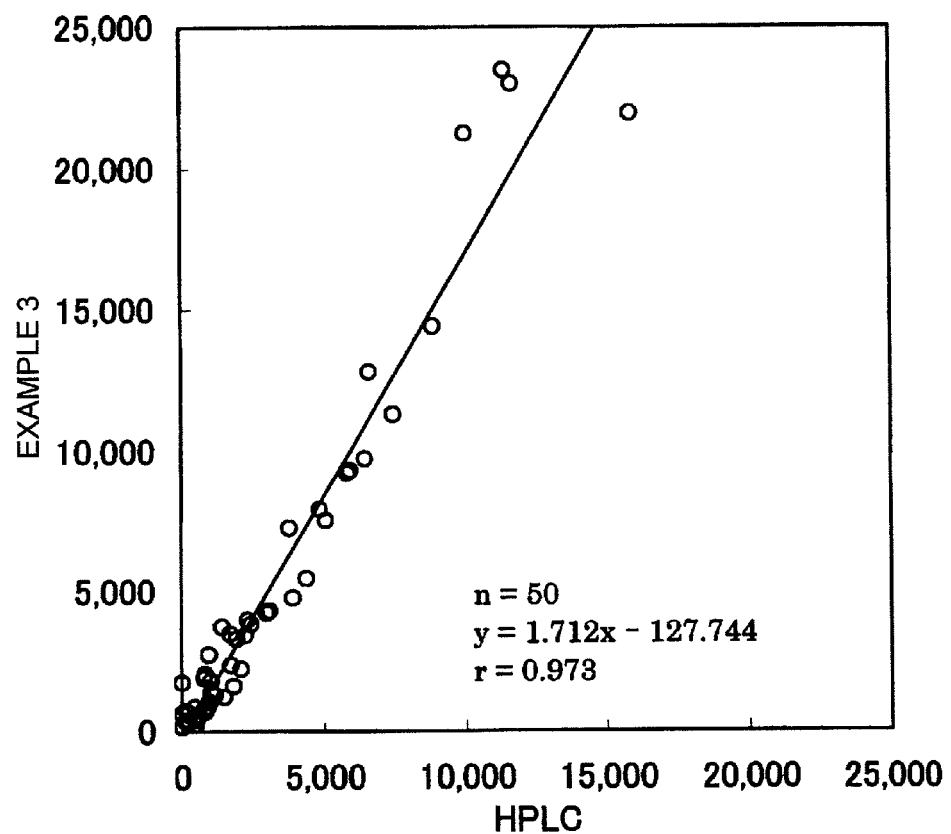
FIG. 3 is a correlation diagram of results measured by HPLC and in Example 3. In the diagram, the vertical axis indicates values obtained by ELISA, and the horizontal axis indicates values obtained by HPLC. The unit is ng/mL in each case.
Figure 4:
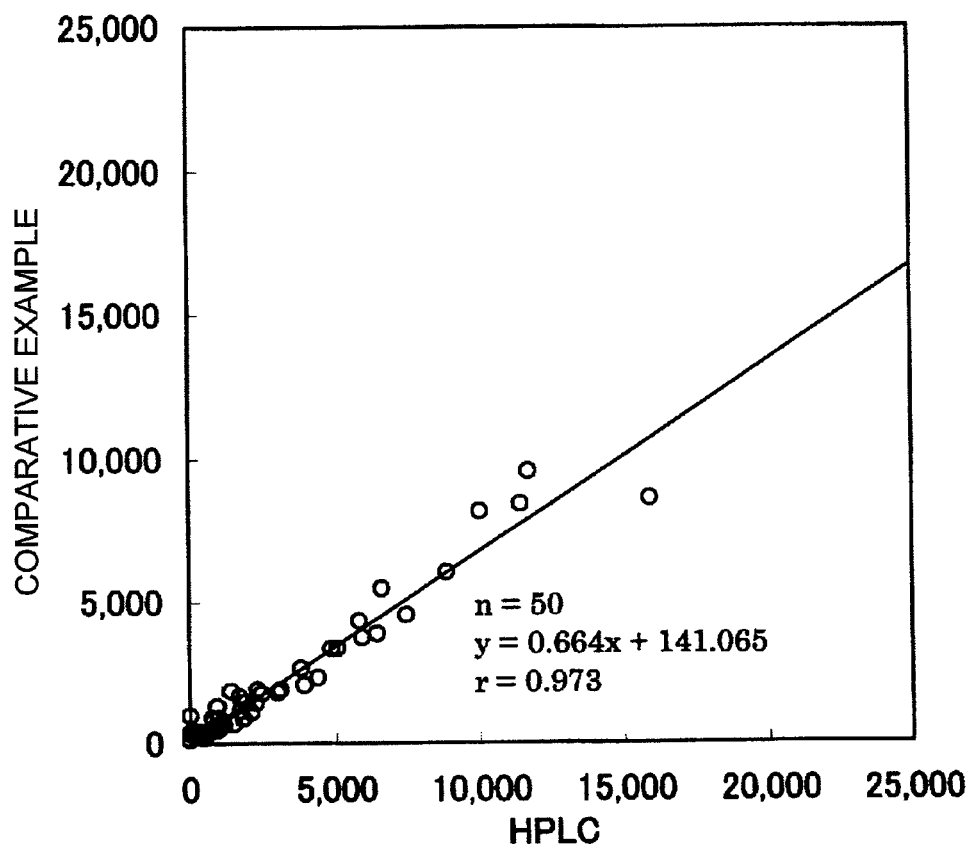
FIG. 4 is a correlation diagram of results measured by HPLC and in the Comparative Example. In the diagram, the vertical axis indicates values obtained by ELISA, and the horizontal axis indicates values obtained by HPLC. The unit is ng/mL in each case.

The present invention is described below.
1. Method for Measuring Equol in Biological Sample by Immunological Method The method of the present invention for measuring equol in a biological sample by an immunological method (hereinafter sometimes referred to as "immunoassay") comprises using S-equol as at least one antigen selected from the group consisting of a standard antigen used for the preparation of a standard curve, and a labeled antigen that competes with equol in a biological sample. The immunoassay of the present invention is described below.

Immunizing Antigen to Prepare Antibody Against S-Equol

Equol, i.e., the target substance of the present invention, is a low-molecular-weight hapten Therefore, equol alone does not possess immunogenicity. Accordingly, in order to obtain an antibody used for immunoassay, it is preferable to prepare an immunizing antigen by synthesizing a complex in which equol is bound to an antigen carrier.

Although the antigen carrier is not limited to any type insofar as the immunizing antigen can be prepared, a polymeric material (having a molecular weight of 10,000 or more, preferably 50,000 to 1,000,000) is preferable, with protein being particularly preferable. Preferable examples of proteins include, but are not limited to, antibodies, bovine serum albumin (BSA), casein, gelatin, ferritin, etc.

Further, the method for binding the hapten to the antigen carrier is not limited, insofar as the hapten and the antigen carrier can be bound together. A preferable method is a covalent bonding.

In the case of a covalent bonding, for example, when a protein is used as the antigen carrier, a succinimide group that has been introduced into the hapten is reacted with the protein or an amino group of the glycoprotein by the N-hydroxysuccinimide-activated ester method; and the hapten can thereby be bound to the antigen carrier. In this case, glutaric dialdehyde method and the like are exemplified as other methods.

Further, in the bonding between the hapten and the antigen carrier, a spacer compound is introduced into the hapten before bonding the hapten to the antigen carrier, in order to expand the distance between the hapten and the antigen carrier. In this way, it is possible to alter the affinity with the antibody, and the specificity of the antibody.

Any spacer compound can be used insofar as the hapten and the antigen carrier can be bound via the spacer compound, and the affinity with the antibody and the specificity of the antibody can be altered by the spacer compound. Examples thereof include carboxymethyl ether (CME), carboxypropyl ether (CPE), carboxybutyl ether (CBE), carboxyphenyl ether (CPhE), and the like, with CME being preferable.

Examples of bindings between the hapten and the antigen carrier via a spacer compound include the later-described equol-CME-protein, equol-CPE-protein, equol-CBE-protein, equol-CPhE-protein, and the like. The equol-CME-protein is prepared in the manner described in a later-described Example. Other immunizing antigens having a spacer compound can be suitably prepared by a person skilled in the art according to the type of the spacer compound used.

Labeled Hapten

A labeled hapten for detecting the presence of an antibody can be prepared in the same manner described above, by using a labeling substance instead of the antigen carrier. The affinity with the antibody to be detected can be adjusted by introducing a spacer compound between the hapten and the labeling substance.

Any known labeling substance can be used as the labeling substance insofar as it does not inhibit an antigen-antibody reaction. Examples of labeling substances include enzymes, radioisotopes, dyes, fluorescent materials, latexes, metal colloids, europium, acridinium, and the like. A preferable labeling substance is selected from the group consisting of enzymes, radioisotopes, dyes, fluorescent materials, latexes, and metal colloids. Further, examples of enzymes include peroxidases, alkaline phosphatase, luciferase, and the like; examples of radioisotopes include $^{125}$I and the like; examples of dyes include cyanine-based dyes and the like; examples of fluorescent materials include FITC, cy3, cy5, and the like; examples of latexes include polystyrene latexes, magnetic latexes, and the like; and examples of metal colloids include gold, silver, platinum, and the like. Of these labeling substances, preferable examples include enzymes, further preferable examples include peroxidases, and particularly preferable examples include horseradish peroxidase, because of the advantage that they can simplify a highly sensitive detection.

Further, examples of spacer compounds used to bind the hapten to the labeling substance include carboxymethyl ether (CME), carboxypropyl ether (CPE), carboxybutyl ether (CBE), carboxyphenyl ether (CPhE), and the like, with CPE being preferable.

Antibody: Primary Antibody

The primary antibody used in the present invention is not limited to any type insofar as it can specifically bind to equol. Either polyclonal or monoclonal antibodies may be used. Further, a fragment of the antibody may be used as the primary antibody insofar as it maintains the specificity to equol. Additionally, an antiserum may also be used as the primary antibody.

The primary antibody used for immunoassay can be prepared by carrying out a known method. For example, the primary antibody can be prepared by the method described below; however, the preparation method is not limited to the following example.

Specifically, a polyclonal antibody can be prepared in the following manner: an immunizing antigen in which equol is bound to an antigen carrier is mixed with Freund's complete adjuvant to prepare an immunizing agent; the prepared immunizing agent is regularly injected subcutaneously and/or intradermally several times into animals such as rabbits, goats, horses, sheep, guinea pigs, chickens, etc., thereby obtaining an antiserum; and the antiserum is purified, diluted, or the like. Examples of immunizing antigens include those described above; and the use of an adjuvant is desirable, although not essential. The antiserum can be collected according to a heretofore known method for preparation. The primary antibody used in the present invention is preferably a rabbit antiserum.

A monoclonal antibody can be prepared in the following manner: an immunizing antigen in which equol is bound to an antigen carrier is mixed with Freund's complete adjuvant to prepare an immunizing agent; the prepared immunizing agent is regularly injected subcutaneously and/or intradermally several times into animals such as mice, rats, etc.; the immunizing antigen alone is then injected intravenously or intraperitoneally; spleen cells prepared from the spleen removed several days later are fused with myeloma cells; and the fused cells are selectively cultured.

The grown fused cells are cultured to produce clones, and a cell line that produces IgG antibodies that specifically bind to equol is selected. Culture supernatant obtained by cultivation of the selected cell line is purified, diluted, or the like. Thereby, a monoclonal antibody to be used for the measurement can be prepared. As in the case of a polyclonal antibody, examples of immunizing antigens include those described above; and the use of an adjuvant is desirable, although not essential.

The primary antibody used in the present invention desirably has a high specificity to S-equol, and a low cross-reactivity with other isoflavones having a similar structure. In particular, because daidzein, dihydrodaidzein, and dehydroequol are factors that lead to erroneous detection of equol in a biological sample, it is desirable to use a primary antibody having a low cross-reactivity with these compounds. Specifically, when the cross-reactivity of the primary antibody used in the present invention with S-equol is assumed to be 100%, the cross-reactivity thereof with daidzein, genistein, glycitein, dihydrodaidzein, and dehydroequol desirably falls in the following ranges:

the cross-reactivity with daidzein: 10% or less, preferably 1% or less, further preferably 0.1% or less;

the cross-reactivity with genistein: 10% or less, preferably 1% or less, further preferably 0.1% or less;

the cross-reactivity with glycitein: 10% or less, preferably 1% or less, further preferably 0.1% or less;

the cross-reactivity with dihydrodaidzein: 20% or less, preferably 5% or less, further preferably 1.1% or less; and the cross-reactivity with dehydroequol: 20% or less, preferably 5% or less, further preferably 1% or less.

The above cross-reactivity can be explained as follows. Specifically, the above cross-reactivity indicates a ratio (%) of the concentration ($IC_{20}$) of unlabeled S-equol at which the binding reaction of labeled S-equol to the anti-equol antibody can be inhibited by 20%, to the concentration ($IC_{20}$) of each isoflavone and the like at which the binding reaction of labeled S-equol to the anti-equol antibody can be inhibited by 20%. More specifically, in the competitive reaction between labeled S-equol and unlabeled S-equol, the concentration of unlabeled S-equol at which the binding of labeled S-equol to the antibody is 80 is determined, assuming that the binding of labeled S-equol alone to the antibody is 100. Similarly, each unlabeled isoflavone and the like are competitively reacted with labeled S-equol, and the concentration of each isoflavone and the like at which binding of labeled S-equol to the antibody is 80 is determined.

The thus-determined ratio (expressed in percentage) between the concentration ($IC_{20}$) of the unlabeled S-equol and the concentration ($IC_{20}$) of each isoflavone and the like is referred to as the cross-reactivity. This is represented by the following formula:

$$\text{Cross-reactivity (\%)} = (IC_{20} \text{ of S-equol}/IC_{20} \text{ of each isoflavone, etc.}) \times 100$$

Herein, the cross-reactivity rate is determined by competitive ELISA, using S-equol as the standard antigen used for the preparation of a standard curve, as well as the labeled antigen that competes with equol in a biological sample.

Further, the concentration of labeled S-equol used for the determination of the cross-reactivity rate may be suitably adjusted to the conditions under which the antigen can be measured at high sensitivity by competitive ELISA. Examples of labeling substances include the above-mentioned enzymes.

More specifically, for example, the cross-reactivity rate is determined according to the same procedure as in the later-described Test Example 2.

It is possible to detect equol in a biological sample at higher sensitivity by using a primary antibody having the above-described specificity, and using S-equol as the standard antigen and/or the labeled antigen that competes with equol in the biological sample.

Antibody: Secondary Antibody

A secondary antibody used in the present invention is an antibody that specifically binds to the primary antibody. The secondary antibody can be prepared according to a known method.

When a rabbit antibody or a rabbit antiserum is used as the primary antibody, a goat anti-rabbit IgG antibody can be preferably used as the secondary antibody.

Further, biotin-avidin/streptavidin binding may be used. In this case, for example, a biotinylated primary antibody may be prepared so as to bind the biotin to avidin/streptavidin immobilized onto a solid phase.

Standard Antigen, and Labeled Antigen that Competes with Equol in Biological Sample Further, in the present invention, when equol in the biological sample is measured using an antibody prepared by the above-described method, it is possible to obtain an accurate measured value by using S-equol as the standard antigen used for the preparation of a standard curve and/or the labeled antigen that competes with equol in the sample. Specifically, although S-equol is used in the present invention as at least one of the standard antigen used for the preparation of a standard curve and the labeled antigen that competes with equol in the sample, it is desirable to use S-equol as both the standard antigen used for the preparation of a standard curve and the labeled antigen that competes with equol in the sample, in view of increasing the accuracy of measurement of equol in a biological sample.

Any heretofore known labeling substance can be used as the labeling substance in the above labeled antigen, insofar as it does not inhibit an antigen-antibody reaction. Examples of labeling substances include enzymes, radioisotopes, dyes, fluorescent materials, latexes, metal colloids, europium, acridinium, and the like. A preferable labeling substance is selected from the group consisting of enzymes, radioisotopes, dyes, fluorescent materials, latexes, and metal colloids. Further, examples of enzymes include peroxidases, alkaline phosphatase, luciferase, and the like; examples of radioisotopes include $^{125}I$ and the like; examples of dyes include cyanine-based dyes and the like; examples of fluorescent materials include FITC, cy3, cy5, and the like; examples of latexes include polystyrene latexes, magnetic latexes, and the like; and examples of metal colloids include gold, silver, platinum, and the like. Of these labeling substances, preferable examples include enzymes, further preferable examples include peroxidases, and particularly preferable examples include horseradish peroxidase, because they can advantageously simplify a highly sensitive detection.

For the purposes of binding the antigen to the labeling substance, and adjusting the affinity and the like between the antigen and the antibody, a spacer compound may be introduced between the antigen and the labeling substance. Examples of spacer compounds used to bind the antigen (S-equol) to the labeling substance include carboxymethyl ether (CME), carboxypropyl ether (CPE), carboxybutyl ether (CBE), carboxyphenyl ether (CPhE), and the like, with CPE being preferable.

Biological Sample

The biological sample for the measurement of equol is not particularly limited to any type, insofar as it is a sample that is derived from living organisms including animals and plants, and from which equol can be measured. Examples thereof include urine, blood (for example, serum and blood plasma), feces, tissue extracts, cell extracts, foodstuffs, etc. The biological samples are preferably derived from a human; and are further preferably urine and blood, and particularly preferably urine derived from a human.

Further, the biological sample used for the measurement of equol may be diluted, if necessary.

Enzyme for Pretreatment (Deconjugation) of Biological Sample

Equol contained in the biological sample is usually present in the conjugate form. Accordingly, the biological sample may be subjected to a pretreatment for deconjugation of equol before being used in an antigen-antibody reaction.

The deconjugation process can be performed using enzymes such as β-glufatase (containing glucuronidase and sulfatase), glucuronidase, sulfatase, etc. More specifically, preferable examples of enzyme solutions used for the deconjugation process include a composition mainly comprising 6% β-glufatase and 0.1 M acetic acid buffer (pH 5.5).

Further, the deconjugation process may be performed prior to or simultaneously with the antigen-antibody reaction. Although the reaction conditions of the deconjugation process are suitably adjusted according to the types of the enzyme, the biological sample used and the like, the deconjugation process is usually performed at 25° C. to 56° C. for 5 minutes to 24 hours.

Diluent for Biological Sample and/or Standard Antigen

A diluent used for dilution of the biological sample and the standard antigen is not limited to any type, insofar as it does not adversely affect the measurement. A diluent used in a general immunological method can be used. Preferable examples of diluents used in the present invention include a mixed solution of sodium chloride and phosphate buffer (pH 7.5) containing bovine serum albumin, 100% charcoal-treated human serum, etc. More specific examples of diluents include a mixed solution of 150 mM sodium chloride and 0.1 M phosphate buffer (pH 7.5) containing 1.0% bovine serum albumin.

Immunological Method for Measuring the Concentration of Equol

Next, specific examples of immunological methods for measuring equol are described below. However, the nature of the present invention is not limited to these examples.

In the present invention, an immunological method for measuring equol is not limited to any type, insofar as it can measure the concentration of equol in a biological sample by an antigen-antibody reaction in which the antigen and the antibody are used. Examples thereof include ELISA, radioimmunoassay, immunochromatographic assay, etc.

Figure 5:
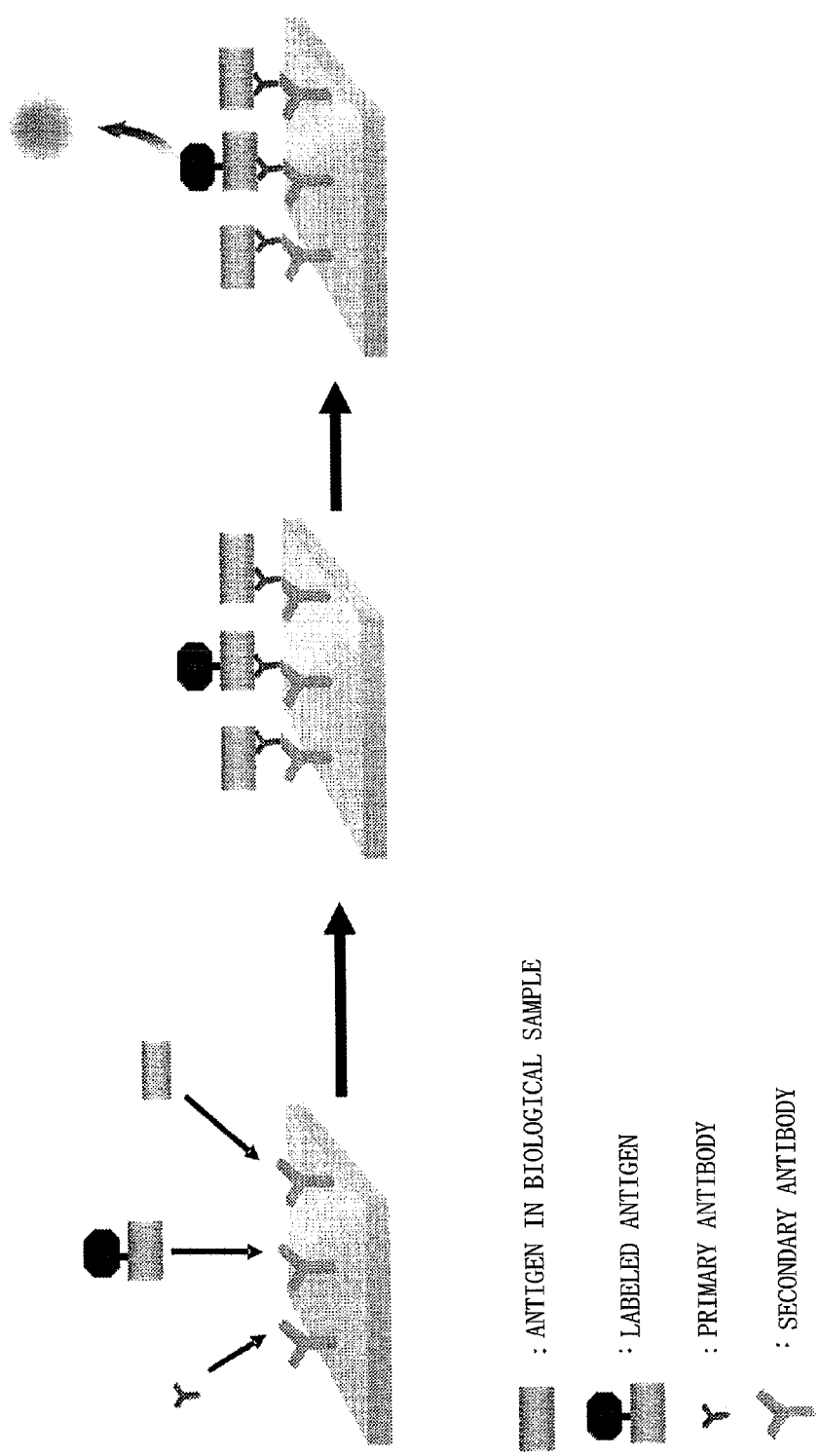
FIG. 5 is a model diagram of competitive ELISA.

When ELISA (Enzyme-Linked Immunosorbent Assay) is used as the immunological method, equol in a biological sample may be measured according to a heretofore known ELISA technique, which may be any of competitive ELISA, sandwich ELISA, and direct ELISA. Competitive ELISA is preferred as a type of ELISA. As a reference, a model of competitive ELISA is shown in FIG. 5.

For example, when competitive ELISA is used, the measurement of equol in a biological sample by ELISA is performed, for example, as follows: a biological sample, an enzyme-labeled antigen (labeled antigen), and a primary antibody are added to wells of a microplate to which a secondary antibody has been immobilized in advance, and the reaction is carried out so as to form a secondary antibody-primary antibody-equol complex. The primary antibody may be simultaneously or separately added to the biological sample and the labeled antigen. After the reaction, the wells are washed with a washing solution, and a substrate for the enzyme is added for the reaction. Subsequently, the reaction is stopped by a reaction stop solution or the like, and the absorbance is measured. Then, the concentration of equol in the sample is calculated from a standard curve generated by measuring the standard antigen in the same manner.

In this case, a heretofore known microplate can be used, and the size and shape of the wells are not limited insofar as the above reaction can be performed. Further, the secondary antibody can be immobilized onto the wells by a heretofore known method. Similarly, a heretofore known substrate that is suitable for the enzyme may be used as the substrate.

Further, in the competitive ELISA, the adding amounts of primary antibody, secondary antibody, and labeled antigen are not limited, insofar as equol in the biological sample can be accurately measured by, the relevant method; and are suitably adjusted according to the general conditions of ELISA. Additionally, in the case of an immunological method other than ELISA, the adding amounts of primary antibody, secondary antibody, and labeled antigen are similarly suitably adjusted according to heretofore known conditions.

Each reaction in ELISA may be carried out according to heretofore known conditions, and is suitably adjusted according to the type of biological samples and the method of ELISA. For example, in the case of competitive ELISA, an antigen-antibody reaction to form a secondary antibody-primary antibody-equol complex is usually carried out at 4° C. to 37° C. for 5 minutes to 24 hours.

More specifically, for the measurement of equol in urine by ELISA (competitive ELISA), a diluent is added to a urine sample to prepare a diluted urine sample; the prepared diluted urine sample, horseradish peroxidase-labeled equol, and diluted anti-equol rabbit antiserum (primary antibody) are added to the wells of a microplate to which a goat anti-rabbit IgG antibody (secondary antibody) has been immobilized in advance; and the reaction is carried out for a certain period of time. After the reaction, the wells are washed, and a colorimetric substrate solution is added to allow the reaction for a certain period of time. After the certain period of time, the reaction is stopped, and the absorbance is measured. Then, the concentration of equol in the sample is calculated from a standard curve generated by measuring the standard antigen in the same manner.

The buffer (antiserum dilution buffer) for diluting antisera is not limited to any type, insofar as it can suitably dilute the antisera and does not adversely affect the measurement. Preferable examples of antiserum dilution buffers used in the present invention include a mixed solution containing sodium chloride, bovine serum albumin, phosphate buffer (pH 7.5) containing Tween 20®, etc. More specifically, examples of antiserum dilution buffers include a mixed solution of 150 mM sodium chloride, 0.5% bovine serum albumin, and 0.01% 0.1 M phosphate buffer (pH 7.5) containing Tween 20®. The antiserum dilution buffer can be used not only in competitive ELISA, but also in different types of ELISA other than competitive ELISA, as well as in various immunological methods. Note that Tween® is a registered trademark.

Measurement of equol in a biological sample by RIA (radioimmunoassay) may also be carried out according to a heretofore known method. The measurement can be performed in the same manner as in ELISA, except that a radioisotope is used as the labeling substance. The following is an example of RIA in which urine is used as the biological sample and $^{125}$I is used as the radioisotope.

A diluent is added to a urine sample to prepare a diluted urine sample; the prepared diluted urine sample, $^{125}$I-labeled S-equol, and diluted anti-equol antibody-producing cell culture supernatant are added to the wells of a microplate to which a goat anti-rabbit IgG antibody has been immobilized in advance; and the reaction is carried out for a certain period of time. After the reaction, the wells are washed; the radioactivity in the wells of the microplate is measured; and the concentration of equol in the sample is calculated from a standard curve generated by measuring the standard antigen in the same manner.

The measurement of equol in a biological sample by an immunochromatographic assay (immunochromatography) may also be carried out according to a heretofore known method. The following is an example technique of an immunochromatographic assay in which urine is used as the biological sample, and gold colloid is used as the radioisotope. Specifically, a gold colloid-labeled anti-equol mouse monoclonal antibody is added to a urine sample to prepare a diluted urine sample, and the diluted urine sample is added dropwise to a sample pad of an immunochromatographic strip to allow the reaction for a certain period of time. After the reaction, coloration caused by the gold colloid labeling substance in a capture area onto which equol is immobilized is measured, and the concentration of equol in the sample is calculated from a standard curve generated by measuring the standard antigen in the same manner.

Further, a method for measuring equol in a biological sample by using a labeled antibody is as follows: equol or its analog bound to an antigen carrier is immobilized to a solid phase, and mixed with an anti-equol rabbit polyclonal antibody labeled with a fluorescent material and a biological sample; the fluorescent material thereby competed with the target substance in the biological sample and bound to the solid phase is washed; the measurement is subsequently carried out; and the concentration of equol in the sample is calculated from a standard curve generated by measuring the standard antigen in the same manner.

Further, open-sandwich ELISA is known as a method for measuring equol in a biological sample by using a labeled antibody fragment. In this measurement method, equol in a sample can be measured, for example, by using a light-chain antigen-binding fragment and a heavy-chain antigen-binding fragment of an anti-equol mouse monoclonal antibody; and forming a polymer into which equol in the biological sample is inserted.

Specifically, the light-chain antigen-binding fragment is immobilized onto a solid phase, and mixed with an alkaline phosphatase-labeled heavy-chain antigen-binding fragment and a biological sample; after washing, the activity of alkaline phosphatase that is bound to the solid phase via equol in the biological sample is measured; and the concentration of equol in the sample is calculated from a standard curve generated by measuring the standard antigen in the same manner.

Alternatively, the light-chain antigen-binding fragment and the heavy-chain antigen-binding fragment may be labeled with different fluorescent materials so as to measure the fluorescence resonance energy transfer phenomenon caused by the formation of a complex via equol in a biological sample; and the concentration of equol in the sample can be calculated from a standard curve generated by measuring the standard antigen in the same manner.

A preferable embodiment of the present invention is ELISA as the immunological method; a further preferable embodiment thereof is competitive ELISA; and a particularly preferable embodiment thereof is competitive ELISA that uses S-equol as both the standard antigen used for the preparation of a standard curve and the labeled antigen that competes with equol in a sample.

2. Kit for Measuring the Concentration of Equol in Biological Sample by Immunological Method The kit of the present invention for measuring the concentration of equol in a biological sample by an immunological method is characterized in that the kit includes S-equol as at least one antigen selected from the group consisting of a standard antigen used for the preparation of a standard curve, and a labeled antigen that competes with equol in the sample. The kit of the present invention may further include a primary antibody that specifically binds to S-equol.

Further, the kit of the present invention may include, if necessary, at least one member selected from the group consisting of a diluent for a biological sample and/or standard antigen, an enzyme solution for deconjugation of an S-equol conjugate in the sample, a plate to which a secondary antibody is immobilized, and a washing solution.

The kit of the present invention may further include a reagent additionally required according to the type of the immunological method employed. For example, when the kit is used in competitive ELISA, the kit may further include at least one member selected from the group consisting of a substrate for a labeling substance in the labeled antigen, a reaction stop solution for stopping the reaction between the labeling substance and the substrate, and a solvent for dissolving the substrate.

Further, when antisera are used in the kit of the present invention, the kit may include an antiserum dilution buffer to be used to dilute the antisera.

Each reagent that may be included in the kit of the present invention is described below.

Standard Antigen

The above-described standard antigen can be similarly used. The standard antigen may be included in the form of a solution in the kit. For example, when S-equol is used as the standard antigen, S-equol may be in the form of a standard equol solution containing S-equol, sodium chloride, and phosphate buffer (pH 7.5) containing bovine serum albumin. Examples of standard equol solutions include a mixture containing 810 ng/mL S-equol, 150 mM sodium chloride, and 0.01 M phosphate buffer (pH 7.5) containing 0.1% bovine serum albumin. Further, examples of different types of standard equol solutions include a mixed solution of S-equol and 100% charcoal-treated human serum, and the like.

Labeled Antigen

The above-described labeled antigen can be similarly used. A preferable example is peroxidase-labeled S-equol, and a particularly preferable example is horseradish peroxidase-labeled S-equol.

Substrate for Labeling Substance

A heretofore known substrate can be used as the substrate for the labeling substance, and the substance is used in a combination with a heretofore known labeling substance. For example, in the case of horseradish peroxidase, examples of the substrate include hydrogen peroxide. The substrate is preferably used after being dissolved in the later-mentioned solvent.

Solvent

A solvent is used in order to dissolve the substance, if necessary. Any heretofore known buffer can be used as the solvent, insofar as it can suitably dissolve the substance and does not adversely affect the measurement. Examples thereof include a citrate buffer, acetic acid buffer, and the like. The solvent can be provided in a form that contains the substrate in advance.

When the substrate is the above-described hydrogen peroxide, a solution obtained by dissolving OPD (o-phenylenediamine dihydrochloride) in the solvent is used as the substrate solution. A suitable embodiment is a substrate solution containing 0.05% hydrogen peroxide solution and 50 mM citrate buffer (pH 5.5) containing 2.2 mg/mL OPD (o-phenylenediamine dihydrochloride).

Antibody: Primary Antibody

The above-described primary antibody can be similarly used. Preferably, an antiserum is used; and further preferably, a rabbit antiserum is used. The antiserum is used after being diluted with the later-described antiserum dissolution buffer, if necessary. The antiserum may be included in the kit in the state of being diluted with the antiserum dilution buffer.

Antibody: Secondary Antibody

The above-described secondary antibody can be similarly used. When a rabbit antibody or a rabbit antiserum is used as the primary antibody, a goat anti-rabbit IgG antibody is preferably used as the secondary antibody. Further, when competitive ELISA is employed, the secondary antibody is preferably immobilized to wells of a microplate. A heretofore known microplate can be used as the microplate, and the immobilization may be carried out according to a heretofore known method.

Antiserum Dilution Buffer

The antiserum dilution buffer is used in order to dilute the above-described antiserum, if necessary. The antiserum dilution buffer is not limited to any type, insofar as it can suitably dilute the antiserum and does not adversely affect the measurement. The above-described antiserum dilution can be similarly used. The antiserum dilution buffer may be included in the kit in the state in which antiserum is diluted.

Enzyme Solution for Pretreatment (Deconjugation) of Biological Sample

The above-described enzyme solution can be similarly used for the pretreatment (deconjugation) of the biological sample.

Diluent for Biological Sample and/or Standard Antigen

The above-described diluent, which is used for the biological sample and the standard antigen, can be similarly used.

Reaction Stop Solution to Stop Reaction Between Labeling Substance and Substrate The reaction stop solution to stop the reaction between the labeling substance and the substrate is not limited to any type, insofar as it can stop the reaction therebetween and does not affect measurement results. A heretofore known reaction stop solution can be used. Examples of reaction stop solutions include sulfuric acid, hydrochloric acid, nitric acid, etc.

Washing Solution

The washing solution is used in order to remove excess biological samples, antibodies, etc. from the wells or the like after the antigen-antibody reaction is finished, and before the substrate is dispensed. The washing solution is not limited to any type, insofar as it can suitably wash and does not adversely affect the measurement. A heretofore known washing solution may be used as is, or by being diluted with purified water or the like. Examples of washing solutions include purified water, solutions in which a surfactant is diluted with a buffer, and the like.

Additionally, the kit of the present invention may also include a handbook that describes protocols for using the kit, a plate for dilution, plate-sealing tape, and the like. Further, a dye for coloration may be added to the above-described solution included in the kit.

Examples of biological samples to be determined by the kit of the present invention include those described above. Further, examples of immunological methods performed using the kit also include the above-described methods, with ELISA being preferable, and competitive ELISA being particularly preferable.

The amounts of the antibody, antigen, solution, and the like contained in the kit are not limited insofar as the concentration of equol in a biological sample can be measured. As described above, the amounts are suitably adjusted according to the general conditions of ELISA and other immunological methods.

3. Method for Determining Equol-Producing Ability of Subject

The method of the present invention for determining the equol-producing ability of a subject (hereinbelow, sometimes referred to as "determination method") comprises the steps of (1) measuring equol in a biological sample derived from a subject who ingested soybean isoflavone, by an immunological method using S-equol as at least one antigen selected from the group consisting of a standard antigen used for the preparation of a standard curve and a labeled antigen that competes with equol in a biological sample, and (2) determining the equol-producing ability of the subject based on the measured value of equol, which is obtained in Step (1). Each step of the determination method of the present invention is described below.

Step (1)

In Step (1), equol in a biological sample derived from a subject who ingested soybean isoflavone is measured by an immunological method using S-equol as at least one antigen selected from the group consisting of a standard antigen used for the preparation of a standard curve, and a labeled antigen that competes with equol in a biological sample.

The biological sample used in Step (1) is a biological sample derived from a subject who ingested soybean isoflavone. Equol is an active metabolite of soybean isoflavone. Therefore, in the case of a subject who has not ingested soybean isoflavone, equol will not be detected; or the measured value of equol will be very low, regardless of the presence of the equol-producing ability of the subject. Accordingly, the subject is required to ingest soybean isoflavone in advance. The amount of soybean isoflavone to be ingested by the subject is not particularly limited. The total amount of soybean isoflavone is, for example, 20 to 70 mg, preferably about 25 to 50 mg. Further, the period of time in which soybean isoflavone is ingested is also not particularly limited. For example, soybean isoflavone is ingested every day for 3 days before collecting biological samples, or 6 to 24 hours before collecting biological samples, preferably 8 to 12 hours before collecting biological samples. Usable soybean isoflavone to be ingested by the subject is in the form of soybean products such as soymilk, soybean isoflavone tablets, soybean bars, fermented soybean paste, soybean curd, boiled soybeans, green soybeans, black beans, tempeh, etc.

The biological sample used in Step (1) may be any of urine, blood (serum, blood plasma), feces, and the like, with urine and blood being preferable, and urine being further preferable.

The measurement of equol by the immunological method in Step (1) is performed according to the above-described section entitled "1. Method for Measuring Equol in Biological Sample by Immunological Method".

Step (2)

In Step 2, the equol-producing ability of a subject is determined based on the measured value of equol, which is obtained in Step (1).

In Step (2), a subject in which equol is detected in his or her biological sample in Step (1) is determined as having the equol-producing ability, and a subject in which equol is not detected in his or her biological sample in Step (1) is determined as not having the equol-producing ability.

Note that, in Step (2), it is preferable to determine whether the measured concentration of equol is less than a cutoff value in order to suppress erroneous determination when determining the presence of the equol-producing ability. Specifically, when the measured concentration of equol in a biological sample is less than the cutoff value, a subject of the biological sample is determined as not having the equol-producing ability; and when the measured concentration of equol in a biological sample is equal to or greater than the cutoff value, a subject of the biological sample is determined as having the equol-producing ability. The cutoff value can be set as follows:

1. The concentration of equol in a biological sample is measured by the above-described immunological method.
2. The concentration of daidzein in the same biological sample is measured. The measurement is performed using an existing measurement method (HPLC, GC-MS, or the like).
3. The log-ratio of the concentration of equol to the concentration of daidzein is calculated for each biological sample. Because equol is a metabolite of daidzein, it is possible to know about how much equol is produced in vivo by calculating the logarithm value.
4. The concentration of S-equol and the concentration of daidzein in the biological sample are measured by HPLC.

5. The log-ratio of the concentration of equol to the concentration of daidzein is calculated for each biological sample based on the measured value in 4 above.

6. The log-ratios obtained in 3 above are compared with the reference value determined by the log-ratios obtained in 5 above, and the results obtained in 3 above are divided into equol production and non-equol production groups. Based on this, the concentration of equol at which the rate of erroneous determination between non-equol producers and equol producers is the lowest is determined, and this concentration is set as the cutoff value.

In regard to 6 above, specifically, in case where when the log-ratios calculated by HPLC, for example, are less than −1.75, the subjects are determined to be non-equol producers and when the ratios are −1.75 or greater, the subjects are determined to be equol producers, this value (−1.75) is used as the reference value (for example, see Setchell and Co, 2006). Then, the log-ratios obtained in 3 above are checked against the reference value, and the subjects are similarly divided into non-equol producers (if the value is less than −1.75) and equol producers (if the value is −1.75 or greater). Subsequently, each concentration of equol measured in 1 above is checked against the classification. Using the above classification as the criteria, the concentration of equol at which the rate of erroneous determination between non-equol producers and equol producers is the lowest is determined; and this concentration is set as the cutoff value.

Further, in Step (2), a subject in which a high concentration of equol is detected from his or her biological sample in Step (1) can be determined as having a high equol-producing ability, and a subject in which a low concentration of equol is detected from his or her biological sample in Step (1) can be determined as having a low equol-producing ability.

EXAMPLES

The presence of two different diastereoisomers of equol, i.e., S-equol and R-equol, is known. The former, i.e., S-equol, is the only type that is present in vivo. Therefore, the measurement method is required to specifically and accurately measure S-equol. Accordingly, a standard antigen and a labeled antigen that affect the measurement by competitive immunoassay were examined.

The measurement methods evaluated and the results thereof are described below.

Test Example 1

Example 1

Measurement by Measurement Kit Using S-Equol as Both Labeled Antigen and Standard Antigen 1. Biological Sample
Urine was used as a biological sample. The number of biological samples was 5.

2. Preparation of Solution of Anti-equol Rabbit Antiserum (Primary Antibody)

Synthesis of Immunizing Antigen

Equol (100 mg) was dissolved in DMSO (400 μL), and methyl bromoacetate (58 μL) and $K_2CO_3$ (140 mg) were added for the reaction at 25° C. for 4 hours. After completion of the reaction, the mixture was adjusted to acidity using hydrochloric acid, extracted using ethyl acetate, dehydrated, and then evaporated to dryness.

Subsequently, the mixture was developed and separated on a thin-layer chromatography (1.05717, Merck, Japan) using chloroformmethanol (19:1) as a developing solvent, and only a fraction where one molecule of CME (carboxymethyl-ether)-methylester was introduced into one molecule of equol was collected.

8N sodium hydroxide was added to the collected equol-CME-methylester, and the mixture was heated at 50° C. for 20 minutes. After heating, the mixture was adjusted to acidity using hydrochloric acid, extracted using ethyl acetate, and evaporated to dryness, thereby obtaining equol-CME-acid.

N-hydroxysuccinimide (NHS) (1.5 mg) and water-soluble carbodiimide (WSC) (1.5 mg) were added to the thus-obtained equol-CME-acid (2 mg). The mixture was dissolved in DMSO (20 μL) and allowed to react at 25° C. for 1 hour, thus obtaining equol-CME-NHS.

Equol-CME-NHS (10 mg/mL DMF solution) (10 μL) was added to 20 mg/mL BSA solution (250 μL, in which bovine serum albumin (20 mg) is dissolved in 50 mM carbonic acid buffer (pH 9.7, 1 mL)) for the reaction at 25° C. for 30 minutes. After completion of the reaction, an unreacted substance was removed by gel filtration, and the resulting solution was used as a stock solution of equol-CME-BSA antigen.

Preparation of Antiserum

The synthesized immunizing antigen equol-CME-BSA (2.5 mg/mL) and Freund's complete adjuvant were mixed in equal amounts to prepare an immunizing agent. The immunizing agent was subcutaneously injected (1 mL per shot, every 3 weeks) into several sites on the back of rabbits. Blood collection was started 12 weeks after the start of immunization, and blood was collected every 3 weeks. After blood was partially collected 5 times, whole blood was collected. Table 1 shows antibody titers of the collected antisera. The antisera obtained by whole blood collection were suitably diluted with an antiserum dilution buffer, and used in the following tests.

Note that, herein, the maximum dilution factor of the individual antiserum in which antibodies can be detected by a heretofore known method was regarded as the antibody titer. The dilution was performed using the later-described antiserum dilution buffer.

TABLE 1

Antibody Titer of Antiserum from Each Blood Collection

| Antiserum | Blood Collection 1 | Blood Collection 2 | Blood Collection 3 | Blood Collection 4 | Blood Collection 5 | Blood Collection 6 (Whole Blood Collection) |
|---|---|---|---|---|---|---|
| No. 11 | 49,000 | 80,000 | 130,000 | 160,000 | 200,000 | 280,000 |

3. Preparation of Goat Anti-Rabbit IgG Antibody (Secondary Antibody) and Antibody Solid-Phase Plate 10 μg/mL goat anti-rabbit IgG antibody solution (100 μL) was added to each well of a 96-well microplate. After the microplate was left to stand at 4° C. for 2 nights, the goat anti-rabbit IgG antibody solution was removed by suction.

0.5 mg/mL bovine serum albumin solution (300 μL) was added to each well of the 96-well microplate from which the solution was removed by suction. After the microplate was left to stand at 4° C. for 18 hours, the bovine serum albumin solution was removed by suction, and the goat anti-rabbit IgG antibody was immobilized to the plate by vacuum-drying.

4. Preparation of Horseradish Peroxidase-Labeled S-Equol (Labeled Antigen that Competes with Equol in Biological Sample)

S-equol (100 mg) was dissolved in DMSO (400 μL), and 4-bromo-n-butylic acid (58 μL) and $K_2CO_3$ (140 mg) were added for the reaction at 25° C. for 4 hours. After completion of the reaction, the mixture was adjusted to acidity using hydrochloric acid, extracted using ethyl acetate, dehydrated, and then evaporated to dryness.

Subsequently, the mixture was developed and separated by thin-layer chromatography (1.05717, Merck, Japan) using chloroformmethanol (19:1) as a developing solvent; and only a fraction where one molecule of CPE (carboxypropylether)-methylester was introduced into one molecule of S-equol was collected.

8N sodium hydroxide was added to the collected S-equol-CPE-methylester, and the mixture was heated at 50° C. for 20 minutes. After heating, the mixture was adjusted to acidity using hydrochloric acid, extracted using ethyl acetate, and evaporated to dryness, thereby obtaining S-equol-CPE-acid.

N-hydroxysuccinimide (NHS) (1.5 mg) and water-soluble carbodiimide (WSC) (1.5 mg) were added to the thus-obtained S-equol-CPE-acid (2 mg). The mixture was dissolved in DMSO (20 μL) and allowed to react at 25° C. for 1 hour, thus obtaining S-equol-CPE-NHS.

S-equol-CPE-NHS (10 mg/mL DMF solution) (10 μL) was added to 20 mg/ml, HRP solution (250 μL, in which horseradish peroxidase (20 mg) is dissolved in 50 mM carbonic acid buffer (pH 9.7, 1 mL)) for the reaction at 25° C. for 30 minutes. After completion of the reaction, an unreacted substance was removed by gel filtration, and the resulting solution was used as a stock solution (labeled antigen solution) of horseradish peroxidase-labeled S-equol solution.

5. Standard Antigen

S-equol was used as a standard antigen. Note that a standard equol solution in the form of a mixed solution of S-equol (0, 30, 90, 270, or 810 ng/mL) and 100% charcoal-treated human serum was used.

6. Biological Sample Diluent and Standard Antigen Diluent

100% charcoal-treated human serum (Seracon II: CD Intergen) was used as a diluent for the biological sample (sample) and the standard antigen.

7. Composition of Antiserum Dilution Buffer 0.1 M phosphate buffer (pH 7.5) containing 150 mM sodium chloride, 0.5% bovine serum albumin, and 0.01% Tween 20® was used as the antiserum dilution buffer. Note that Tween® is a registered trademark.

8. Composition of Washing Solution 0.3 mM phosphate buffer (pH 7.5) containing 100 mM sodium chloride and 0.025% Tween 20® was used as a washing solution.

9. Composition of Enzyme Solution 0.1 M acetic acid buffer (pH 5.5) containing 6% β-glufatase (Nippon Biotest Laboratories) was used as an enzyme solution.

10. Substrate 50 mM citrate buffer (pH 5.5) containing 0.05% hydrogen peroxide solution and 2.2 mg/mL OPD (o-phenylenediamine dihydrochloride) was used as a substrate (substrate solution).

11. Reaction Stop Solution 3N sulfuric acid was used as a reaction stop solution.

12. Measurement of Equol Using Biological Sample

A diluent (200 μL) was added to a urine sample (20 μL) to prepare an 11-fold diluted urine sample. A mixed solution (50 μL) of the 11-fold diluted urine sample (20 μL), enzyme, and labeled antigen (the ratio of enzyme solution to labeled antigen solution is 10:1) was added to the plate wells containing immobilized anti-rabbit IgG goat antibody. The plate was stirred, and then left to stand at 25° C. for 30 minutes. Subsequently, the anti-equol rabbit antiserum solution (50 μL) was added thereto, and the mixture was stirred and then left to stand at 25° C. for 1 hour.

After the reaction solution was removed from the plate wells containing immobilized goat anti-rabbit IgG antibody, the wells were washed 3 times using the washing solution. After washing, the substrate (100 μL) was added to the plate wells containing immobilized goat anti-rabbit IgG antibody, and the plate was left to stand at 25° C. for 30 minutes. Subsequently, the reaction stop solution (100μ) was added to the plate wells containing immobilized goat anti-rabbit IgG antibody, and the absorption at the wavelength of 490 nm was measured. Then, the concentration of equol in the sample was calculated from a standard curve generated from a dilution series (prepared using a standard diluent) of the standard antigen, which was measured in the same manner.

Example 2

Measurement by Measurement Kit Using S-Equol as Labeled Antigen

Example 2 was conducted in the same manner as in Example 1, except that the "standard antigen" in Example 1 was changed from S-equol to equol (a mixture of S-equol and R-equol).

Example 3

Measurement by Measurement Kit Using S-Equol as Standard Antigen

Example 3 was conducted in the same manner as in Example 1, except that the S-equol in the "preparation of horseradish peroxidase-labeled S-equol" in Example 1 was changed to equol (a mixture of S-equol and R-equol), as described below.

Preparation of Horseradish Peroxidase-Labeled Equol

Equol (100 mg) was dissolved in DMSO (400 μL), and 4-bromo-n-butylic acid (58 μL) and $K_2CO_3$ (140 mg) were added for the reaction at 25° C. for 4 hours. After completion of the reaction, the mixture was adjusted to acidity using hydrochloric acid, extracted using ethyl acetate, dehydrated, and then evaporated to dryness.

Subsequently, the mixture was developed and separated on a thin-layer chromatography (1.05717, Merck, Japan) using chloroformmethanol (19:1) as a developing solvent; and only a fraction where one molecule of CPE (carboxypropylether)-methylester was introduced into one molecule of equol was collected.

8N sodium hydroxide was added to the collected equol-CPE-methylester, and the mixture was heated at 50° C. for 20 minutes. After heating, the mixture was adjusted to acidity using hydrochloric acid, extracted using ethyl acetate, and evaporated to dryness, thereby obtaining equol-CPE-acid.

N-hydroxysuccinimide (NHS) (1.5 mg) and water-soluble carbodiimide (WSC) (1.5 mg) were added to the thus-obtained equol-CPE-acid (2 mg). The mixture was dissolved in DMSO (20 μL) and allowed to react at 25° C. for 1 hour, thus obtaining equol-CPE-NHS.

Equol-CPE-NHS (10 mg/ml, DMF solution) (10 μL) was added to 20 mg/mL HRP solution (250 μL, in which horse-radish peroxidase (20 mg) is dissolved in 50 mM carbonic acid buffer (pH 9.7, 1 mL)) for the reaction at 25° C. for 30 minutes. After completion of the reaction, an unreacted substance was removed by gel filtration, and the resulting solution was used as a stock solution of horseradish peroxidase-labeled equol solution.

Comparative Example

Measurement by Measurement Kit Using Equol as Both Labeled Antigen and Standard Antigen Comparative Example was conducted in the same manner as in Example 1, except that the S-equol as the "standard antigen" in Example 1 was changed to the equol described in Example 2; and the S-equol in the "preparation of horseradish peroxidase-labeled S-equol" was changed to the equol described in Example 3.

Example 4

Comparison of Measured Values Against HPLC (Panel Sample)

Five urine samples in which the concentration of equol is known by HPLC were measured according to Example 1, Example 2, Example 3, and the Comparative Example. Table 2 shows the results thereof. Table 3 shows the ratio of each measured value, assuming that the measured value by HPLC is 100%.

TABLE 2

Measured Values of 5 Urine Samples (ng/mL)

| | HPLC | Example 1 | Example 2 | Example 3 | Comparative Example |
|---|---|---|---|---|---|
| Urine Sample A | 507 | 541 | 659 | 808 | 418 |
| Urine Sample B | 1,775 | 1,703 | 2,175 | 1,844 | 906 |
| Urine Sample C | 4,008 | 3,961 | 5,044 | 5,353 | 2,385 |
| Urine Sample D | 8,360 | 7,436 | 9,332 | 7,691 | 3,251 |
| Urine Sample E | 12,540 | 11,447 | 13,230 | 12,315 | 4,877 |

TABLE 3

Ratio (%) of Measured Values of 5 Urine Samples to Measured Values by HPLC

| | Example 1 | Example 2 | Example 3 | Comparative Example |
|---|---|---|---|---|
| Urine Sample A | 107 | 130 | 159 | 82 |
| Urine Sample B | 96 | 123 | 104 | 51 |
| Urine Sample C | 99 | 126 | 134 | 60 |
| Urine Sample D | 89 | 112 | 92 | 39 |
| Urine Sample E | 91 | 106 | 98 | 39 |

While the ratio of the measurement results from the Comparative Example to the measurement results from HPLC is in the range from 39% to 82%, the ratios obtained from Examples 1, 2, and 3 are in the ranges of from 89% to 107%, 106% to 130%, and 92% to 159%, respectively. The use of S-equol as the standard antigen and/or the labeled antigen narrowed the discrepancy between the measured values obtained with and without HPLC.

Example 5

Correlation with HPLC (Measured Value)

Fifty urine samples in which the concentration of equol is known by HPLC were measured in the same manner described in Example 1, Example 2, Example 3, and the Comparative Example. Correlations between the results from these Examples and the measurement results from HPLC are respectively shown in FIG. 1, FIG. 2, FIG. 3, and FIG. 4. A subject was required to ingest soybean isoflavone (26 mg of isoflavone aglycone) the day before the measurement, and the first urine excreted in the morning was used as the urine sample.

Although the measurement results from the Comparative Example show a high correlation (correlation coefficient r=0.973), the slope of the regression equation is 0.664, i.e., almost half of the measured value obtained by HPLC.

On the other hand, the measurement result from Example 1 shows a high correlation (correlation coefficient r=0.974), and the slope of the regression equation is 1.067, i.e., comparable to the measured value obtained by HPLC. Therefore, it was determined that the accuracy was increased more in Example 1 than in the Comparative Example.

Note that the measurement results from Example 2 show a high correlation (correlation coefficient r=0.987); and that the slope of the regression equation is 1.594, i.e., higher than the measured value obtained by HPLC.

Note that the measurement results from Example 3 show a high correlation (correlation coefficient r=0.973); and that the slope of the regression equation is 1.712, i.e., higher than the measured value obtained by HPLC. The graph (FIG. 3) shows a large variation in the measurement results. A discrepancy in the measured values was observed, especially in the measured values in the high range.

Test Example 2

Cross-Reactivity

In this Test Example, the cross-reactivity of the primary antibody was examined for the case where competitive ELISA was employed and S-equol was used as both the standard antigen and the labeled antigen. Specifically, the cross-reactivity was examined as follows.

1. Sample

Each of the isoflavones and the like shown in the later-described Table 4 was dissolved in 100% charcoal-treated human serum, and the resulting solution was used as a sample.

2. Primary Antibody

An anti-equol rabbit antiserum was used as the primary antibody, as in Example 1. The antiserum was suitably diluted with the later-described antiserum dilution buffer, and used in the test.

3. Secondary Antibody

A goat anti-rabbit IgG antibody was used as a secondary antibody, as in Example 1. The antibody was immobilized to a solid phase as in Example 1, thus preparing a plate containing immobilized goat anti-rabbit IgG antibody.

4. Labeled Antigen that Competes with Equol in Biological Sample

Horseradish peroxidase-labeled S-equol was used as a labeled antigen, as in Example 1.

5. Standard Antigen

S-equol was used as a standard antigen, as in Example 1. Note that a standard equol solution in the forth of a mixed solution of S-equol (0, 30, 90, 270, or 810 ng/mL) and 100% charcoal-treated human serum was used.

6. Diluent for Sample and Standard Antigen

100% charcoal-treated human serum (Seracon II: CD Intergen) was used as a diluent for the sample and the standard antigen.

7. Antiserum Dilution Buffer 0.1 M phosphate buffer (pH 7.5) containing 150 mM sodium chloride, 0.5% bovine serum albumin, and 0.01% Tween 20® was used as an antiserum dilution buffer.

8. Washing Solution 0.3 mM phosphate buffer (pH 7.5) containing 100 mM sodium chloride and 0.025% Tween 20® was used as a washing solution.

9. Enzyme Solution 0.1 M acetic acid buffer (pH 5.5) containing 6% β-glufatase (Nippon Biotest Laboratories) was used as an enzyme solution.

10. Substrate 50 mM citrate buffer (pH 5.5) containing 0.05% hydrogen peroxide solution and 2.2 mg/mL OPD (o-phenylenediamine dihydrochloride) was used as a substrate (substrate solution).

11. Reaction Stop Solution 3N sulfuric acid was used as a reaction stop solution.

12. Procedure to Examine Cross-Reactivity

A concentration dilution series was prepared for each of the isoflavones and the like, and for unlabeled S-equol. The adsorption by each of the isoflavones and the like, and the adsorption by unlabeled S-equol in the competitive reaction were measured from when the concentrations of these substances were 0 to when the concentrations of these substances were added in excess amounts. Each of the thus-obtained measured values was checked against a standard curve obtained from the dilution series of the standard antigen (S-equol), so as to compare the inhibition of the reaction based on each calculated value. Thereby, the concentration ($IC_{20}$) of each of the isoflavones and the like, as well as the concentration ($IC_{20}$) of unlabeled S-equol, at which the binding reaction of labeled S-equol to the anti-equol antibody is inhibited by 20%, were determined.

The competitive reaction was performed using competitive ELISA by a procedure similar to that in Example 1. Further, horseradish peroxidase was used as a labeling substance.

The ratio (expressed in percentage) of the thus-obtained concentration of each of the isoflavones and the like to the thus-obtained concentration of unlabeled S-equol was regarded as the cross-reactivity. This is represented by the following formula:

Cross-reactivity (%)=($IC_{20}$ of S-equol/$IC_{20}$ of each isoflavone, etc.)×100

Table 4 shows the results.

TABLE 4

| Isoflavones and the Like | Cross-reactivity Rate |
| --- | --- |
| S-Equol | 100.00% |
| R-Equol | 13.24% |
| Daidzein | 0.08% |
| Genistein | 0.05% |
| Glycitein | 0.03% |
| Glycitin | 0.02% |
| Estradiol | 0.01% |
| Daidzin | 0.06% |
| Genistin | 0.06% |
| Biochanin A | 0.11% |
| Formononetin | 0.21% |
| Dihydrodaizein | 1.03% |
| Apigenin | 0.00% |
| Luteolin | 0.00% |
| Dehydroequol | 0.33% |

According to the results, when the cross-reactivity of the primary antibody with S-equol is assumed to be 100%, the cross-reactivity thereof with R-equol is 13.24%, the cross-reactivity thereof with daidzein before being metabolized is 0.08%, the cross-reactivity thereof with dihydrodaizein is 1.03%, the cross-reactivity thereof with dehydroequol is 0.33%, and the cross-reactivity thereof with daidzin is 0.06%. The results show that the primary antibody also has a significantly low cross-reactivity with various other substances. This means that S-equol can be specifically detected and measured by the method of the present invention, and further by the kit of the present invention.

Further, for example, when Labmaster Equol TR-FIA, which is a heretofore known kit manufactured by Labmaster, is used, the cross-reactivity rate with daidzein is 0.8% (see labmaster.fi/products/tr-fia-kitS-equol-tr-fia.htm), and the cross-reactivity of the kit is 10 times as high as that of the present kit. Furthermore, when Labmaster Equol TR-FIA is used, the cross-reactivity rate with dehydroequol is 42.3%, and the cross-reactivity rate with dihydrodaidzein is 4.0%. Thus, the present kit is considered to exhibit significantly higher specificity, compared to a heretofore known kit.

Further, in the past, an article (Duncan C. S. Talbot, et al. Clinical Chemistry 53: 748-756, 2007) that discusses research that uses a monoclonal antibody reported that the cross-reactivity rate with daidzein was <0.04%. This indicates that although the present invention uses an antiserum as the primary antibody, it exhibits specificity that is equivalent to that of the monoclonal antibody.

Test Example 3

Correlation with Liquid Chromatography/Tandem Mass Spectrometer (LC/MS/MS)

In this Test Example, the correlation with an LC/MS/MS method was examined for the case where competitive ELISA was employed, and where S-equol was used as both the standard antigen and the labeled antigen. Specifically, the correlation was examined as follows.

1. Biological Sample

Sera of 10 males before and after they ingested isoflavone were used as biological samples.

2. Primary Antibody

The same anti-equol rabbit antiserum as that used in Example 1 was used a primary antibody. The antiserum was suitably diluted with the later-described antiserum dilution buffer, and used in the test.

3. Secondary Antibody

The same goat anti-rabbit IgG antibody as that used in Example 1 was used as a secondary antibody. The antibody was immobilized to a solid phase as in Example 1, thus preparing a plate containing immobilized goat anti-rabbit IgG antibody.

4. Labeled Antigen that Competes with Equol in Biological Sample

The same labeled antigen solution of horseradish peroxidase-labeled S-equol as that used in Example 1 was used as the labeled antigen.

5. Standard Antigen

S-equol was used as a standard antigen as in Example 1. Note that 810 ng/mL S-equol was suitably diluted with the standard antigen diluent, and the resulting solution was used as a standard equol solution.

6. Standard Antigen Diluent

100% charcoal-treated human serum was used as a diluent for the standard antigen.

7. Antiserum Dilution Buffer 0.1 M phosphate buffer (pH 7.5) containing 150 mM sodium chloride, 0.5% bovine serum albumin, and 0.01% Tween 20® was used as an antiserum dilution buffer.

8. Washing Solution 0.3 mM phosphate buffer (pH 7.5) containing 100 mM sodium chloride and 0.025% Tween 20® was used as a washing solution.

9. Enzyme Solution 0.1 M acetic acid buffer (pH 5.5) containing 6% β-glufatase (Nippon Biotest Laboratories) was used as an enzyme solution.

10. Substrate 50 mM citrate buffer (pH 5.5) containing 0.05% hydrogen peroxide solution and 2.2 mg/mL OPD (o-phenylenediamine dihydrochloride) was used as a substrate (substrate solution).

11. Reaction Stop Solution 3N sulfuric acid was used as the reaction stop solution.

12. Procedure to Measure the Concentration of Equol

A mixed solution (50 μL) of serum sample (20 μL), enzyme, and labeled antigen (the ratio of enzyme solution to labeled antigen solution is 10:1) was added to the plate wells containing immobilized goat anti-rabbit IgG antibody, and the plate was stirred and then left to stand at 25° C. for 30 minutes. Subsequently, the anti-equol rabbit antiserum solution (50 μL) was added thereto, and the mixture was stirred and then left to stand at 25° C. for 1 hour.

After the reaction solution was removed from the plate wells containing immobilized goat anti-rabbit IgG antibody, the wells were washed 3 times using the washing solution. After washing, the substrate (100 μL) was added to the plate wells containing immobilized goat anti-rabbit IgG antibody, and the plate was left to stand at 25° C. for 30 minutes. Subsequently, the reaction stop solution (100μ) was added to the plate wells containing immobilized goat anti-rabbit IgG antibody, and the absorption at the wavelength of 490 nm was measured. Then, the concentration of equol in the sample was calculated from a standard curve generated from a dilution series (prepared using a standard diluent) of the standard antigen, which was measured in the same manner.

Figure 6:
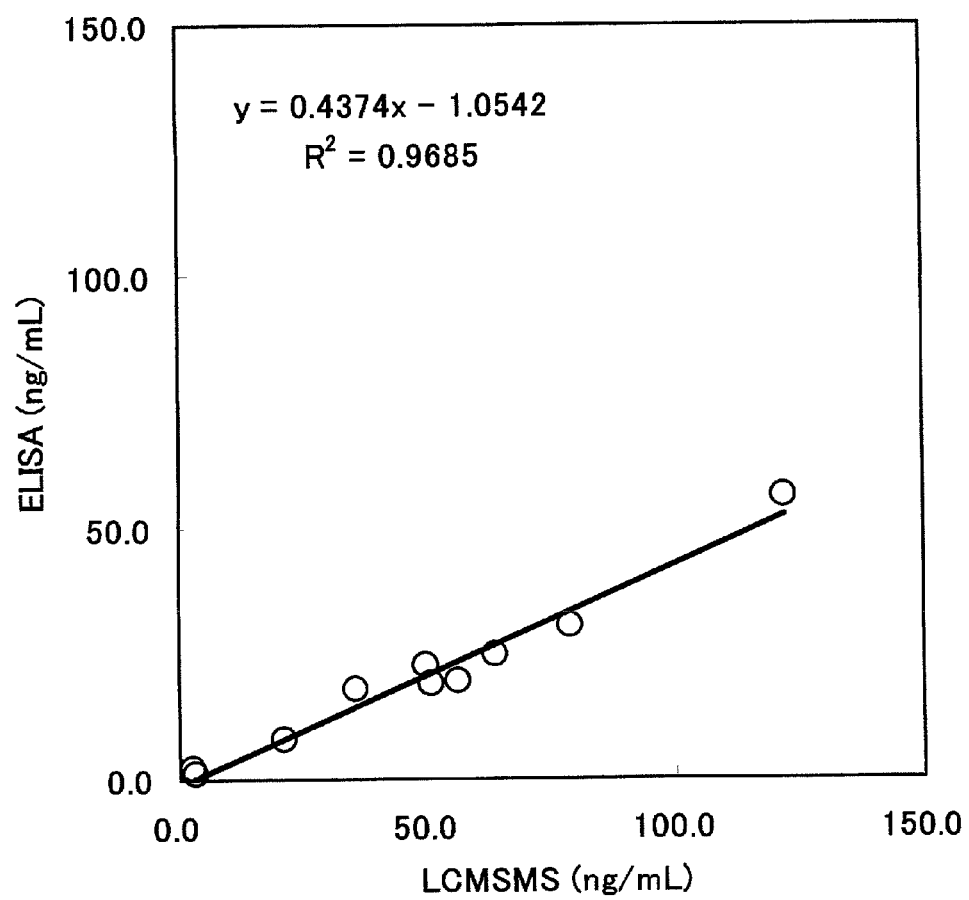
FIG. 6 is a correlation diagram of results regarding the concentration of equol measured by LC/MS/MS, and by an immunoassay of the present invention described in Test Example 3.

Further, the concentration of equol in the same biological sample was measured using a liquid chromatography/tandem mass spectrometer (LC/MS/MS). The thus-obtained results were compared. Table 5 and FIG. 6 show the correlations of the results.

TABLE 5

|  | LCMSMS (ng/mL) | ELISA (ng/mL) |
| --- | --- | --- |
| Serum Sample 1 | 3.5 | 1.0 |
| Serum Sample 2 | 2.8 | 2.0 |
| Serum Sample 3 | 21.0 | 7.8 |
| Serum Sample 4 | 35.6 | 17.9 |
| Serum Sample 5 | 50.9 | 19.0 |
| Serum Sample 6 | 49.5 | 22.8 |
| Serum Sample 7 | 63.9 | 24.9 |
| Serum Sample 8 | 55.9 | 19.2 |
| Serum Sample 9 | 78.7 | 30.2 |
| Serum Sample 10 | 121.9 | 56.3 |
| Correlation Coefficient |  | 0.984 |

Table 5 shows that the absolute values of the measurement results of the serum samples obtained in Example 4 are lower (less than half) than those obtained by LC/MS/MS. However, Table 5 shows a high correlation coefficient (0.984).

Test Example 4

Determination 1 of S-Equol Producer/Non-S-Equol Producer (Cutoff Value Setting)

In the present test example, the cutoff value was set in the following manner.

A subject was required to ingest soybean isoflavone (about 25 mg of isoflavone aglycone) during the evening meal the day before the measurement, and the first urine excreted in the morning at least 6 hours after the ingestion was used as the urine sample. The number of subjects was 244 (76 males and 168 females), and the number of biological samples was 432.

Figure 7:
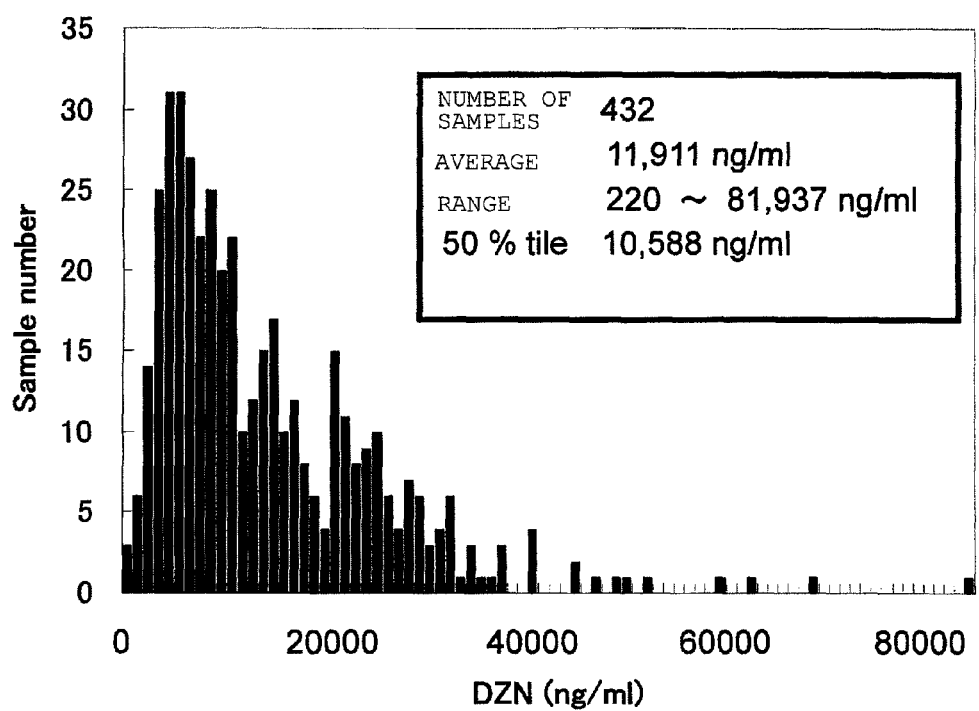
FIG. 7 shows the concentration of daidzein in urine measured using HPLC.

FIG. 7 shows the measurement results regarding the concentration of daidzein (DZN). The concentration of DZN was measured using HPLC. A sufficient amount of DZN was detected in the first urine excreted in the morning by the ingestion of isoflavone the day before the measurement. Accordingly, it was decided that it is possible to determine S-equol producers and non-S-equal producers.

Figure 8:
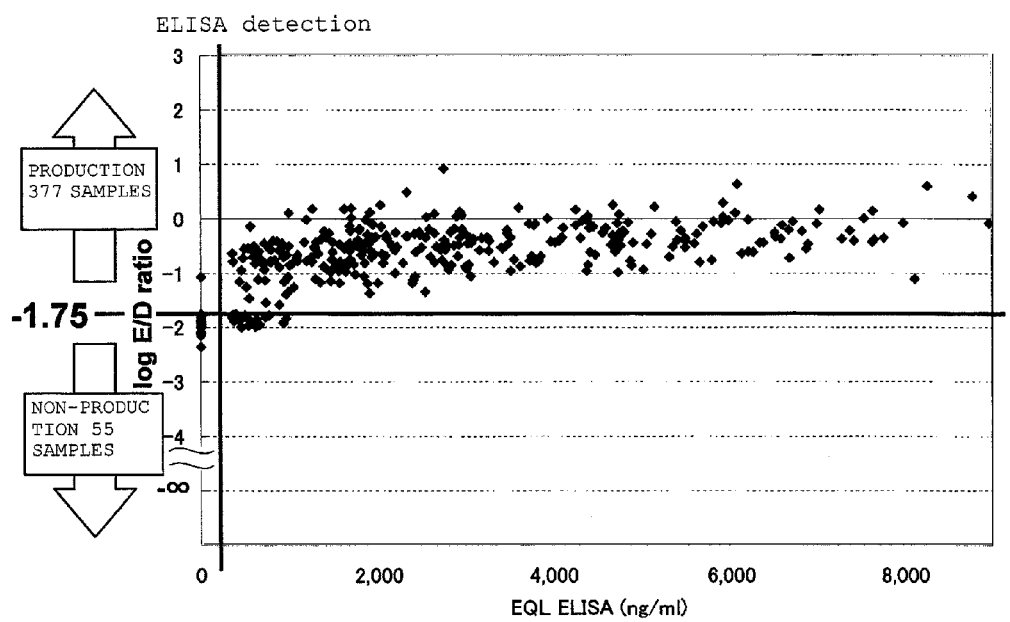
FIG. 8 shows plots of EQL ELISA versus Log E/D ratio.

Next, the concentration (EQL ELISA) of equol (EQL) in the urine was measured by ELISA. The detection limit was 330 ng/ml. At the same time, the log-ratio (Log E/D ratio) of the concentration of EQL to the concentration of DZN was calculated based on the results from HPLC. FIG. 8 shows plots between the EQL ELISA and the Log E/D ratio. Note that with the Log E/D ratio, a value of −1.75 (Kenneth D. R. Stechell and Sindey J. cole, J. Nutr. 136: 2188-2193, August 2006) was used as the reference value, and the subjects with a value of −1.75 or greater were determined to be equol producers; the subjects with a value less than −1.75 were determined to be non-equol producers.

Based on the above, the concentration of equol at which the rate of erroneous determination between non-equol producers and equol producers is lowest, i.e., the cutoff value, was examined. Table 6 shows the results of the examination. Note that, according to HPLC, the number of biological samples determined to be the producers was 377, and the number of biological samples determined to be the non-producers was 55.

TABLE 6

| | (1) Erroneous Determination in Which Non-Equol Producers are Determined to be Equol Producers The Number of Samples Without Equol-Producing Ability: 55 | | (2) Erroneous Determination in Which Equol Producers are Determined to be Non-Equol Producers The Number of Samples With Equol-Producing Ability: 377 | | Total Erroneous Determination Total Number of Samples: 432 | |
|---|---|---|---|---|---|---|
| Cutoff Value (ng/mL) | The Number of Samples | Erroneous Determination Rate (%) | The Number of Samples | Erroneous Determination Rate (%) | The Number of Samples | Total Erroneous Determination Rate (%) |
| 330 | 23 | 41.8 | 2 | 0.5 | 25 | 42.3 |
| 400 | 16 | 29.1 | 4 | 1.1 | 20 | 30.2 |
| 450 | 14 | 25.5 | 5 | 1.3 | 19 | 26.8 |
| 500 | 11 | 20.0 | 8 | 2.1 | 19 | 22.1 |
| 550 | 9 | 16.4 | 11 | 2.9 | 20 | 19.3 |
| 600 | 8 | 14.5 | 15 | 4.0 | 23 | 18.5 |
| 650 | 5 | 9.1 | 17 | 4.5 | 22 | 13.6 |
| 700 | 4 | 7.3 | 20 | 5.3 | 24 | 12.6 |
| 750 | 3 | 5.5 | 25 | 6.6 | 28 | 12.1 |
| 800 | 2 | 3.6 | 29 | 7.7 | 31 | 11.3 |
| 850 | 2 | 3.6 | 31 | 8.2 | 33 | 11.9 |
| 900 | 2 | 3.6 | 35 | 9.3 | 37 | 12.9 |
| 950 | 1 | 1.8 | 39 | 10.3 | 40 | 12.2 |
| 1000 | 0 | 0.0 | 45 | 11.9 | 45 | 11.9 |

According to Table 6, the rate of erroneous determination between equol producers and non-equol producers was lowest when the concentration of equol was 800 ng/ml. Accordingly, in this case, the cutoff value was set to 800 ng/ml.

Test Example 5

Determination 2 of S-Equol Producer/Non-S-Equol Producer (Cutoff Value Setting)

The cutoff value as the criterion for determining S-equol producers and non-S-equol producers was set in the same manner as in Test Example 4.

Note that the number of biological samples in the immunoassay was 713. Further, undetectable values were treated as "0". Table 7 shows the results of the examination.

According to Table 7, the rate of erroneous determination between equol producers and non-equol producers was lowest when the concentration of equol was 650 ng/ml. Accordingly, in this case, the cutoff value was set to 650 ng/ml.

Test Example 6

Determination 3 of S-Equol Producer/Non-S-Equol Producer

The cutoff value as the criterion for determining between S-equol producers and non-S-equol producers was set in the same manner as in Test Example 4.

Note that the number of biological samples in the immunoassay was 118. Table 8 shows the results of the examination.

TABLE 7

| | (1) Erroneous Determination in Which Non-Equol Producers are Determined to be Equol Producers The Number of Samples Without Equol-Producing Ability: 337 | | (2) Erroneous Determination in Which Equol Producers are Determined to be Non-Equol Producers The Number of Samples With Equol-Producing Ability: 376 | | Total Erroneous Determination Total Number of Samples: 713 | |
|---|---|---|---|---|---|---|
| Cutoff Value (ng/mL) | The Number of Samples | Erroneous Determination Rate (%) | The Number of Samples | Erroneous Determination Rate (%) | The Number of Samples | Total Erroneous Determination Rate (%) |
| 330 | 63 | 18.9 | 1 | 0.3 | 64 | 19.2 |
| 400 | 45 | 13.6 | 3 | 0.8 | 48 | 14.4 |
| 450 | 35 | 10.7 | 4 | 1.1 | 39 | 11.7 |
| 500 | 29 | 8.6 | 7 | 1.9 | 36 | 10.4 |
| 550 | 22 | 6.5 | 10 | 2.7 | 32 | 9.2 |
| 600 | 18 | 5.3 | 14 | 3.7 | 32 | 9.0 |
| 650 | 13 | 3.8 | 16 | 4.3 | 29 | 8.1 |
| 700 | 11 | 3.3 | 19 | 5.1 | 30 | 8.3 |
| 750 | 9 | 2.7 | 24 | 6.4 | 33 | 9.0 |
| 800 | 6 | 1.8 | 28 | 7.4 | 34 | 9.2 |
| 850 | 5 | 1.5 | 30 | 8.0 | 35 | 9.5 |
| 900 | 4 | 1.2 | 34 | 9.0 | 38 | 10.2 |
| 950 | 3 | 0.9 | 38 | 10.1 | 41 | 11.0 |
| 1000 | 1 | 0.3 | 44 | 11.7 | 45 | 12.0 |
| 1050 | 1 | 0.3 | 47 | 12.5 | 48 | 12.8 |
| 1100 | 1 | 0.3 | 50 | 13.3 | 51 | 13.6 |
| 1150 | 1 | 0.3 | 50 | 13.3 | 51 | 13.6 |
| 1200 | 1 | 0.3 | 53 | 14.1 | 54 | 14.4 |
| 1250 | 1 | 0.0 | 54 | 14.4 | 55 | 14.4 |

TABLE 8

| Cutoff Value (ng/mL) | (1) Erroneous Determination in Which Non-Equol Producers are Determined to be Equol Producers The Number of Samples Without Equol-Producing Ability: 55 | | (2) Erroneous Determination in Which Equol Producers are Determined to be Non-Equol Producers The Number of Samples With Equol-Producing Ability: 63 | | Total Erroneous Determination Total Number of Samples: 118 | |
|---|---|---|---|---|---|---|
| | The Number of Samples | Erroneous Determination Rate (%) | The Number of Samples | Erroneous Determination Rate (%) | The Number of Samples | Total Erroneous Determination Rate (%) |
| 330 | 23 | 41.8 | 1 | 1.6 | 24 | 43.4 |
| 400 | 16 | 29.1 | 1 | 1.6 | 17 | 30.7 |
| 450 | 14 | 25.5 | 2 | 3.2 | 16 | 28.6 |
| 500 | 11 | 20.0 | 3 | 4.8 | 14 | 24.8 |
| 550 | 9 | 16.4 | 3 | 4.8 | 12 | 21.1 |
| 600 | 8 | 14.5 | 3 | 4.8 | 11 | 19.3 |
| 650 | 5 | 9.1 | 3 | 4.8 | 8 | 13.9 |
| 700 | 4 | 7.3 | 3 | 4.8 | 7 | 12.0 |
| 750 | 3 | 5.5 | 3 | 4.8 | 6 | 10.2 |
| 800 | 2 | 3.6 | 3 | 4.8 | 5 | 8.4 |
| 850 | 2 | 3.6 | 3 | 4.8 | 5 | 8.4 |
| 900 | 2 | 3.6 | 4 | 6.3 | 6 | 10.0 |
| 950 | 1 | 1.8 | 4 | 6.3 | 5 | 8.2 |
| 1000 | 0 | 0.0 | 4 | 6.3 | 4 | 6.3 |

According to Table 8, the rate of erroneous determination between equol producers and non-equol producers was the lowest when the concentration of equol was 1,000 ng/ml. Accordingly, in this case, the cutoff value was set to 1,000 ng/ml.

INDUSTRIAL APPLICABILITY

When soybean processed products are ingested with expectations for the anti-estrogenic effect and the estrogen-like effect, the presence of these effects is determined by measuring the concentration of equol in urine or blood. However, a method using instrumental analysis such as HPLC and the like to accurately measure equol takes time and effort to process multiple samples, and thus is not suitable for daily measurements.

However, according to the present invention, equol in urine and blood can be quickly and accurately measured, and it is possible to infer the effects of the ingestion of soybean processed products, including determining the effect of administration of safe Lactobacillus preparations that produce equol.

The invention claimed is:

1. A method for determining an S-equol-producing ability of a subject, comprising the steps of
    (1) measuring S-equol in a biological sample derived from a subject who has ingested soybean isoflavone, by an immunological method comprising:
        (a) mixing said sample with labeled S-equol, contacting the resulting mixture with an antibody that binds S-equol, and detecting the amount of the labeled S-equol bound to the antibody, wherein said antibody is a diluted antiserum, and wherein when S-equol is present in said sample, the S-equol in said sample competes with the labeled S-equol for binding to said antibody; and
        (b) calculating the amount of S-equol in said sample, by comparing the detected amount of the labeled S-equol bound to the antibody to a standard curve, wherein said standard curve has been prepared by mixing labeled S-equol with different amounts of a standard, contacting the resulting mixtures with an antibody that binds S-equol, and detecting the amount of the labeled S-equol bound to the antibody, wherein said standard is S-equol, and wherein said standard competes with the labeled S-equol for binding to said antibody; and
    (2) making a determination according to (i) or (ii):
        (i) determining that said subject has an S-equol-producing ability when S-equol is detected in said sample, or determining that said subject does not have an S-equol-producing ability when S-equol is not detected in said sample; or
        (ii) determining that said subject has an S-equol-producing ability when S-equol is detected in said sample in an amount equal to or greater than a pre-determined cut-off value, or determining that said subject does not have an S-equol-producing ability when S-equol is not detected in said sample, or is detected in an amount less than a pre-determined cut-off value, wherein the biological sample is at least one member selected from the group consisting of urine, blood, and feces.

2. The determination method according to claim 1, wherein, in step (1), an S-equol conjugate in the biological sample is measured without being deconjugated.

3. The determination method according to claim 1, wherein the subject is determined as having an S-equol-producing ability when the S-equol concentration in the sample is 650 ng/ml or more.

4. The determination method according to claim 1, wherein in step (2), the determination is made according to (ii).

5. The determination method according to claim 1, which does not comprise a step of comparing a concentration of daidzein and the concentration of S-equol in the sample.

6. The determination method according to claim 1, wherein the measuring step of step (1) is performed in three hours or less.

7. The determination method according to claim 1, wherein an anti-equol antibody whose cross-reactivity with daidzein is 10% or less; cross-reactivity with genistein is 10% or less; cross-reactivity with glycitein is 10% or less; cross-reactivity with dihydrodaidzein is 20% or less; and cross-reactivity with dehydroequol is 20% or less, when the cross-reactivity with S-equol is assumed to be 100%, is used as a primary antibody.

8. The determination method according to claim 1, wherein a labeling substance of the labeled antigen is at least one member selected from the group consisting of enzymes, radioisotopes, dyes, fluorescent materials, latexes, and metal colloids.

9. The determination method according to claim 1, wherein the immunological method is at least one type selected from the group consisting of ELISA, radioimmunoassay, and immunochromatographic assay.

10. The determination method according to claim 1, wherein the biological sample is at least one member selected from the group consisting of urine and blood.

* * * * *